(12) United States Patent
Craig

(10) Patent No.: US 8,280,505 B2
(45) Date of Patent: Oct. 2, 2012

(54) VAGUS NERVE STIMULATION METHOD

(75) Inventor: Arthur D. Craig, Phoenix, AZ (US)

(73) Assignee: Catholic Healthcare West, Phoenix, AZ (US)

( * ) Notice: Subject to any disclaimer, the term of this patent is extended or adjusted under 35 U.S.C. 154(b) by 0 days.

(21) Appl. No.: 12/400,893

(22) Filed: Mar. 10, 2009

(65) Prior Publication Data

US 2009/0171405 A1  Jul. 2, 2009

Related U.S. Application Data

(63) Continuation of application No. 11/693,421, filed on Mar. 29, 2007, now Pat. No. 8,150,508.

(60) Provisional application No. 60/787,680, filed on Mar. 29, 2006.

(51) Int. Cl.
*A61N 1/36* (2006.01)

(52) U.S. Cl. ............. 607/2; 607/1; 607/6; 607/7; 607/9; 607/45; 607/115; 607/118; 607/119

(58) Field of Classification Search .................. 607/1–2, 607/6–7, 9, 45, 115, 118–119
See application file for complete search history.

(56) References Cited

U.S. PATENT DOCUMENTS

| | | | |
|---|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |

(Continued)

FOREIGN PATENT DOCUMENTS

CA  2339971  6/2004

(Continued)

OTHER PUBLICATIONS

Non-final U.S. Office Action, notification date Mar. 16, 2010 U.S. Appl. No. 11/693,499.

(Continued)

*Primary Examiner* — Carl H Layno
*Assistant Examiner* — Deborah Malamud
(74) *Attorney, Agent, or Firm* — Ballard Spahr LLP

(57) ABSTRACT

An implanted electrical signal generator delivers a novel exogenous electrical signal to a vagus nerve of a patient. The vagus nerve conducts action potentials originating in the heart and lungs to various structures of the brain, thereby eliciting a vagal evoked potential in those structures. The exogenous electrical signal simulates and/or augments the endogenous afferent activity originating from the heart and/or lungs of the patient, thereby enhancing the vagal evoked potential in the various structures of the brain. The exogenous electrical signal includes a series of electrical pulses organized or patterned into a series of microbursts including 2 to 20 pulses each. No pulses are sent between the microbursts. Each of the microbursts may be synchronized with the QRS wave portion of an ECG. The enhanced vagal evoked potential in the various structures of the brain may be used to treat various medical conditions including epilepsy and depression.

30 Claims, 10 Drawing Sheets

U.S. PATENT DOCUMENTS

| | | |
|---|---|---|
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 5,025,807 A | 6/1991 | Zabara |
| 5,081,987 A | 1/1992 | Nigam |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Dorfmeister et al. |
| 6,002,966 A | 12/1999 | Loeb et al. |
| 6,016,449 A | 1/2000 | Fischell et al. |
| 6,041,258 A | 3/2000 | Cigaina et al. |
| 6,073,048 A * | 6/2000 | Kieval et al. .................. 607/17 |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki et al. |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja et al. |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |

| Patent/Pub No. | Date | Name |
|---|---|---|
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 7,422,555 B2 | 9/2008 | Zabara |
| 7,454,245 B2 | 11/2008 | Armstrong et al. |
| 7,603,174 B2 * | 10/2009 | De Ridder .......... 607/55 |
| 7,634,317 B2 | 12/2009 | Ben-David et al. |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0036780 A1 | 2/2003 | Barrett et al. |
| 2003/0040774 A1 | 2/2003 | Terry, Jr. et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0195574 A1 | 10/2003 | Osorio et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0024428 A1 | 2/2004 | Barrett et al. |
| 2004/0036377 A1 | 2/2004 | Mezinis |
| 2004/0039424 A1 | 2/2004 | Merritt et al. |
| 2004/0039427 A1 | 2/2004 | Barrett et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0254612 A1 | 12/2004 | Ezra et al. |
| 2004/0254616 A1 * | 12/2004 | Rossing et al. ........ 607/42 |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065553 A1 | 3/2005 | Ben Ezra et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |

| Publication No. | Date | Inventor |
|---|---|---|
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0197675 A1 | 9/2005 | David et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0251220 A1 | 11/2005 | Barrett et al. |
| 2005/0251222 A1 | 11/2005 | Barrett et al. |
| 2005/0261542 A1 | 11/2005 | Riehl |
| 2005/0267542 A1 | 12/2005 | David et al. |
| 2005/0267550 A1 | 12/2005 | Hess et al. |
| 2005/0272280 A1 | 12/2005 | Osypka |
| 2005/0277872 A1 | 12/2005 | Colby, Jr. et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja |
| 2006/0015153 A1 | 1/2006 | Gliner et al. |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja |
| 2006/0079936 A1 | 4/2006 | Boveja |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0100668 A1 | 5/2006 | Ben-David et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173494 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0200208 A1 | 9/2006 | Terry, Jr. et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224188 A1 | 10/2006 | Libbus et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0247719 A1 | 11/2006 | Maschino et al. |
| 2006/0247722 A1 | 11/2006 | Maschino et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271108 A1 | 11/2006 | Libbus et al. |
| 2006/0271409 A1 | 11/2006 | Rosenfeld et al. |
| 2006/0293720 A1 | 12/2006 | DiLorenzo |
| 2006/0293721 A1 | 12/2006 | Tarver et al. |
| 2007/0021786 A1 | 1/2007 | Parnis et al. |
| 2007/0027486 A1 | 2/2007 | Armstrong et al. |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073346 A1 | 3/2007 | Corbucci et al. |
| 2007/0073355 A1 | 3/2007 | DiLorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner et al. |
| 2007/0123946 A1 | 5/2007 | Masoud |
| 2007/0135855 A1 | 6/2007 | Foshee et al. |
| 2007/0142862 A1 | 6/2007 | DiLorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | DiLorenzo et al. |
| 2007/0156179 A1 | 7/2007 | Karashurov |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |

| | | |
|---|---|---|
| 2007/0173901 A1 | 7/2007 | Reeve |
| 2007/0179534 A1 | 8/2007 | Firlik et al. |
| 2007/0179558 A1 | 8/2007 | Gliner et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0255374 A1 | 11/2007 | Kolafa et al. |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | DiLorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson et al. |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0054795 A1 | 2/2009 | Misczynski et al. |
| 2009/0076567 A1 | 3/2009 | Fowler et al. |

FOREIGN PATENT DOCUMENTS

| | | |
|---|---|---|
| EP | 0402683 | 5/1990 |
| EP | 0713714 | 7/1995 |
| EP | 1070518 | 5/2000 |
| EP | 1145736 | 10/2001 |
| EP | 1304135 A2 | 4/2003 |
| EP | 1486232 A2 | 12/2004 |
| EP | 1595497 | 11/2005 |
| EP | 1120130 | 12/2005 |
| EP | 1634617 A1 | 3/2006 |
| EP | 1647300 | 4/2006 |
| EP | 1745818 | 1/2007 |
| GB | 2026870 | 2/1980 |
| GB | 2079610 | 1/1982 |
| WO | 9301862 | 2/1993 |
| WO | 9302744 | 2/1993 |
| WO | 9321824 A1 | 11/1993 |
| WO | 9400185 | 1/1994 |
| WO | 9400188 | 1/1994 |
| WO | WO 9417771 | 8/1994 |
| WO | 9956822 | 11/1999 |
| WO | WO 0040143 | 12/1999 |
| WO | WO 01008749 | 6/2000 |
| WO | WO 0064480 | 11/2000 |
| WO | WO 9825688 | 4/2001 |
| WO | WO 0064336 | 6/2002 |
| WO | WO 03085546 | 10/2003 |
| WO | WO 2004036377 | 4/2004 |
| WO | WO 2004064918 | 8/2004 |
| WO | WO 2004069330 | 8/2004 |
| WO | WO 2004071575 | 8/2004 |
| WO | WO 2004075982 | 9/2004 |
| WO | WO 03076010 | 12/2004 |
| WO | WO 2004112894 | 12/2004 |
| WO | WO 2005007120 | 1/2005 |
| WO | WO 2005007232 | 1/2005 |
| WO | WO 2005028026 A1 | 3/2005 |
| WO | WO 2005053788 | 6/2005 |
| WO | WO 2005067599 | 7/2005 |
| WO | WO 2005101282 | 10/2005 |
| WO | WO 2006014760 | 2/2006 |
| WO | WO 2006019822 | 2/2006 |
| WO | WO 2006050144 | 5/2006 |
| WO | WO 0105467 | 9/2006 |
| WO | 2006118793 | 11/2006 |
| WO | WO 2006122148 | 11/2006 |
| WO | WO 2007066343 A2 | 6/2007 |
| WO | WO 2007072425 | 6/2007 |
| WO | WO 2007124126 | 11/2007 |
| WO | WO 2007124190 | 11/2007 |
| WO | WO 2007124192 | 11/2007 |
| WO | WO 2007142523 | 12/2007 |

OTHER PUBLICATIONS

Craig, A.D. (BUD), Mechanisms of Thalamic Pain; Central Neuropathic Pain; Focus on Poststroke Pain, 2007, IASP Press, Seattle, Washington.

Craig, A.D. (BUD), Vagal Input to Lateral Area 3a in Cat Cortex; J. Neurophysiol 90, Jan. 15, 2003, 143-154; USA.

Ito, S.; Craig, A.D., Forebrain Projections of the Vagal Responsive Site in the Thalamic Parafascicular Nucleus in Monkeys; Nov. 13, 2005; Presentation 305.2, Washington D.C.

Ito, S.; Craig, A.D., Forebrain Projections from Different Portions of the Vagal Responsive Region in the Thalamic Parafascicular Nucleus in Monkeys; Oct. 15, 2006; Program 166.9/AA28, USA.

Ito, S.; Craig, A.D., Vagal-Evoked Activity in the Parafascicular Nucleus of the Primate Thalamus; J. Neurophysiol 94, May 31, 2005, 2976-2982; USA.
Restriction Requirement in U.S. Appl. No. 11/693,421, Mar. 18, 2010.
First Office Action in U.S. Appl. No. 11/693,451, Apr. 21, 2010.
First Office Action in U.S. Appl. No. 12/401,026, Apr. 19, 2010.
Israeli Patent Application No. 194406: Official Action issued by the State of Israel Department of Justice on Oct. 20, 2010, 4 pages.
Israeli Patent Application No. 194407: Official Action issued by the State of Israel Department of Justice on Oct. 21, 2010, 4 pages.
Examination Report in European Patent Application No. 07759728.4, Mailing Date: Apr. 27, 2010.
Examination Report in European Patent Application No. 07759722.7, Mailing Date: Apr. 27, 2010.
Examination Report in European Patent Application No. 07759710.2, Mailing Date: Apr. 13, 2010.
Examination Report in European Patent Application No. 07759728.4, Mailing Date: Aug. 8, 2009.
Examination Report in European Patent Application No. 07759710.2, Mailing Date: Jun. 10, 2009.
Examination Report in European Patent Application No. 07759722.7, Mailing Date: Jun. 16, 2009.
Examiner's First Report in Australian Patent Application No. 2007233135, Mailing Date: Aug. 9, 2010.
Office Action in U.S. Appl. No. 11/693,421, Mailing Date: Aug. 12, 2010.
Examination Report in Australian Patent Application No. 2007233205, Mailing Date: Aug. 9, 2010.
Final Office Action in U.S. Appl. No. 11/693,499, Mailing Date: Sep. 28, 2010.
Final Office Action in U.S. Appl. No. 11/693,451, Mailing Date: Oct. 22, 2010.
Final Office Action in U.S. Appl. No. 12/401,026, Mailing Date: Nov. 15, 2010.
Bachman, D.,S. et al.; "*Effects of Vagal Volleys and Serotonin on Units of Cingulate Cortex in Monkeys*; " Brain Research , vol. 130 (1977). pp. 253-269.
Bohning, D.E., et al.; "*Feasibility of Vagus Nerve Stimulation—Synchronized Blood Oxygenation Level-Dependent Functional MRI*;" A Journal of Clinical and Laboratory Research: Investigative Radiology; vol. 36, No. 8 (Aug. 2001); pp. 470-479.
Boon, Paul, et al.; "*Programmed and Magnet-Induced Vagus Nerve Stimulation for Refractory Epilepsy*; " Journal of Clinical Neurophysiology vol. 18 No. 5; (2001); pp. 402-407.
Clark, K.B., et al.; "*Posttraining Electrical Stimulation of Vagal Afferents with Concomitant Vagal Efferent Inactivation Enhances Memory Storage Processes in the Rat*; " Neurobiology of Learning and Memory, vol. 70, 364-373 (1998) Art. No. NL983863.
Clark, K.B., et al.; "*Enhanced Recognition Memory Following Vagus Nerve Stimulation in Human Subjects*;" Nature Neuroscience, vol. 2, No. 1, (Jan. 1999) pp. 93-98.
Craig, A.D. (BUD); "*Distribution of Trigeminothalamic and Spinothalamic Lamina I Terminations in the Macaque Monkey*; " The Journal of Comparative Neurology, vol. 477, pp. 119-148 (2004).
DeGiorgo, Christopher M., et al.; "*Vagus Nerve Stimulation: Analysis of Device Parameters in 154 Patients During the Long-Term XE5 Study;*" Epilepsia, vol. 42, No. 8; pp. 1017-1020 (2001).
Devous, Michael D., et al.; "*Effects of Vagus Nerve Stimulation on Regional Cerebral Blood Flow in Treatment-Resistant Depression*;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.
Dodrill, Ph.D., et al.; "*Effects of Vagal Nerve Stimulation on Cognition and Quality of Life in Epilepsy*;" Epilepsy and Behavior, vol. 2 (2001); pp. 46-53.
Fanselow, E. E., et al.; "*Reduction of Pentylenetetrazole-Induced Seizure Activity in Awake Rats by Seizure-Triggered Trigeminal Nerve Stimulation*;" The Journal of Neuroscience, vol. 20, No. 21; (Nov. 2000); pp. 8160-8168.
Fromes, G. A.et al.; "Clinical Utility of On-Demand Magnet use with Vagus Nerve Stimulation;" AES Proceedings, p. 117.
George, M.S., et al.; "*Open Trial of VNS Therapy in Severe Anxiety Disorders*;" 156th American Psychiatric Association Annual Meeting; May 17-22, 2003.
George, M.S., et al.; "*Vagus Nerve Stimulation: A New Tool for Brain Research and Therapy*;" Society of Biological Psychiatry vol. 47 (2000) pp. 287-295.

Hallowitz, R.A., et al.; "*Effects of Vagal Tolleys on Units of Intralaminar and Juxtalaminar Thalamic Nuclei in Monkeys*; " Brain Research, vol. 130 (1977), pp. 271-286.
Harry, J.D., et al.; "*Balancing Act: Noise is the Key to Restoring the Body's Sense of Equilibrium*;" IEEE Spectrum (Apr. 2005)pp. 37-41.
Henry, T.R., et al.; "*Brain Blood-Flow Alterations Induced by Therapeutic Vagus Nerve Stimulation in Partial Epilepsy: I. Acute Effects at High and Low Levels of Stimulation;* " Epilepsia vol. 39, No. 9; pp. 984-990 (1998).
Henry, MD, T.R.; "*Therapeutic Mechanisms of Vagus Nerve Stimulation*" Neurology, vol. 59 Suppl. 4 (Sep. 2002); pp. S3-S14.
King, M.D., "*Effects of Short-Term Vagus Nerve Stimulation (VNS) on FOS Expression in Rat Brain Nuclei*" 58th Annual Scientific Convention of the Society of Biological Psychiatry, (May 2003).
Klapper, M.D., et al., "*VNS Therapy Shows Potential Benefit in Patients with Migraine and Chronic Daily Headache After 3 to 6 Months of Treatment (Preliminary Results)*" 45th Annual Scientific Meeting of the American Headache Society (Jun. 2003).
Koo, B., "*EEG Changes With Vagus Nerve Stimulation*" Journal of Clinical Neurophysiology, vol. 18 No. 5 (Sep. 2001); pp. 434-441.
Labar, D., "*Vagus Nerve Stimulation for 1 Year in 269 patients on Unchanged Antiepilectic Drugs*" Seizure vol. 13, (2004) pp. 392-398.
Lockard et al., "*Feasibility and Safety of Vagal Stimulation in Monkey Model;* " Epilepsia, vol. 31 (Supp. 2) (1990), pp. S20-S26.
Liebman, K.M. et al.; "*Improvement in Cognitive Function After Vagal Nerve Stimulator Implantation;* " Epilepsia, vol. 39, Suppl. 6 (1998) 1 page.
Malow, B.A., et al.; "*Vagus Nerve Stimulation Reduces Daytime Sleepiness in Epilepsy Patients*" Neurology 57 (2001) pp. 879-884.
McClintock, P., "*Can Noise Actually Boost Brain Power*" Physics World Jul. 2002; pp. 20-21.
Mori, T., et al.; "*Noise-Induced Entrainment and Stochastic Resonance in Human Brain Waves*" Physical Review Letters vol. 88, No. 21 (2002); pp. 218101-1-218101-4.
Rugg-Gunn, F.J., et al.; "*Cardiac Arrhythmias in Focal Epilepsy: a Prospective Long-Term Study*" www.thelancet.com vol. 364 (2004) pp. 2212-2219.
Rutecki, P.; "*Anatomical, Physiological, and Theoretical Basis for the Antiepileptic Effect of Vagus Nerve Stimulation*" Epilepsia, vol. 31 Suppl. 2; S1-S6 (1990).
Sahin, M.; et al.; "*Improved Nerve Cuff Electrode Recordings with Subthreshold Anodic Currents*; " IEEE Transactions on Biomedical Engineering, vol. 45, No. 8 (Aug. 1998) pp. 1044-1050.
Schachter, S.C., et al.; "*Progress in Epilepsy Research: Vagus Nerve Stimulation;* " Epilepsia, vol. 39, No. 7 (1998) pp. 677-686.
Tatum, W.O., et al.; "*Ventricular Asystole During Vagus Nerve Stimulation for Epilepsy in Humans*" American Academy of Neuroloyggy (1999) p. 1267 (See also pp. 1117, 1166, and 1265).
Tatum, W.O., et al.; "*Vagus Nerve Stimulation and Drug Reduction*" Neurology, vol. 56, No. 4 (Feb. 2001) pp. 561-563.
Terry et al.; "*The Implantable Neurocybernetic Prosthesis System*", Pacing and Clinical Electrophysiology, vol. 14, No. 1 (Jan. 1991), pp. 86-93.
Tubbs, R.S., et al.; "*Left-Sided Vagus Nerve Stimulation Decreases Intracranial Pressure Without Resultant Bradycardia in the Pig: A Potential Therapeutic Modality for Humans*" Child's Nervous System Original Paper; Springer-Verlag 2004.
Valdez-Cruz, A., et al.; "*Chronic Stimulation of the Cat Vagus Nerve Effect on Sleep and Behavior*" Progress in Neuro-Psychopharmacology & Biological Psychiatry, vol. 26 (2002) pp. 113-118.
Vonck, K., et al. "*The Mechanism of Action of Vagus Nerve Stimulation for Refractory Epilepsy—The Current Status*", Journal of Neurophysiology, vol. 18 No. 5 (2001), pp. 394-401.
Ward, H., M.D., et al.; "*Treatment-Refractory Obsessive-Compulsive Disorder: Potential Benefit of VNS Therapy*" 23rd Annual Conference of the Anxiety Disorders Association of America (2007).
Woodbury, et al., "*Vagal Stimulation Reduces the Severity of Maximal Electroshock Seizures in Intact Rats. Use of a Cuff Electrode for Stimulating and Recording*"; Pacing and Clinical Electrophysiology, vol. 14 (Jan. 1991), pp. 94-107.
Zabara, J. "*Inhibition of Experimental Seizures in Canines by Repetivie Vagal Stimulation*" Epilepsia vol. 33, No. 6 (1992); pp. 1005-1012.

* cited by examiner

Every 6 seconds     Every 2 seconds     Every 0.5 seconds

VAGUS NERVE STIMULATION METHOD

CROSS REFERENCE TO RELATED APPLICATION(S)

This application is a continuation of U.S. application Ser. No. 11/693,421, filed Mar. 29, 2007, now U.S. Pat. No. 8,150,508, and which itself claims the benefit of U.S. Provisional Application No. 60/787,680, filed Mar. 29, 2006.

BACKGROUND OF THE INVENTION

1. Field of the Invention

The present invention is directed generally to neurostimulation of the vagus nerve, and more particularly to an improved apparatus and method for vagus nerve stimulation therapy using heart rate variability synchronization, patterned electrical pulses inside a pulse burst, and electroencephalogram ("EEG") based optimization.

2. Description of the Related Art

Vagus nerve stimulation ("VNS") (for example, VNS Therapy™ by Cyberonics, Inc.) is an FDA-approved method for alleviating treatment-resistant epilepsy and depression.

Vagus nerve stimulation was initially developed and approved by the FDA for the treatment of refractory partial onset epilepsy. Recently, it has been reported that the use of VNS in human patients with epilepsy is associated with an improvement in mood. As a consequence, VNS has also been approved as a treatment for refractory depression (treatment resistant depression).

VNS typically involves implanting a nerve stimulating electrode on the left or right vagus nerve in the neck. The electrode is connected to a subcutaneous pacemaker-like control unit that generates an electrical nerve stimulating signal. A Vagus Nerve Stimulator ("VNS stimulator") is an example of an implantable stopwatch-sized, pacemaker-like control unit device configured to electrically stimulate the vagus nerve leading to the brain.

Conventional VNS is generally applied every 5 minutes in a 7 second to one minute burst (see FIG. 3A for a portion of an exemplary burst) including a pulse train of uniformly spaced apart pulses having a pulse current amplitude of about 0.5 mA to about 2.0 mA). The pulses are delivered at about 20 Hz to about 50 Hz. Each of the pulses may have a width of about 0.5 milliseconds. VNS is currently approved to treat epileptic seizures and depression when drugs have been ineffective.

Consequently, a need exists for methods of delivering electrical stimulation to the vagus nerve. Further, a need exists for improved electrical signals that increase the efficacy of VNS.

SUMMARY OF THE INVENTION

In one embodiment, the invention includes a method of treating a medical condition by detecting a portion of the QRS wave of the patient's cardiac signal and after detecting the portion of the QRS wave, delivering a microburst comprising 2 to 20 electrical pulses to the patient's vagus nerve. Each of the microbursts may have duration of less than about 100 milliseconds. In particular embodiments, the interpulse intervals separating the pulses are about 3 milliseconds to about 12 milliseconds. In alternate embodiments, the interpulse intervals are less than about 40 milliseconds. In various embodiments, the sum of the interpulse intervals is less than about 40 milliseconds, and in further embodiments, less than about 60 milliseconds. In further embodiments, the method includes waiting a predetermined delay period after the detection of the portion of the QRS wave before generating the microburst.

In another embodiment, the invention includes an exogenous electrical signal delivered to a patient's vagus nerve and adapted to treat a medical condition present in the patient by enhancing the vagal evoked potential in the patient's brain. The exogenous electrical signal includes a series of microbursts each having about 2 to about 20 electrical pulses. In some embodiments, the exogenous electrical signal includes a series of microbursts each having a duration less than about one second. The invention also includes an implantable device configured to apply the inventive exogenous electrical signal.

In further embodiments, the microbursts of the exogenous electrical signal may be synchronized with the R wave portion of the patient's cardiac cycle. In particular embodiments, each of the microbursts of the exogenous electrical signal occur after a selected R wave portion. In various embodiments, each of the microbursts occurs less than about 1000 milliseconds after the selected R wave portion. The pulses of the microbursts may be spaced to simulate the endogenous afferent activity occurring at a particular time in the cardiac cycle. Further, each of the microbursts may be delayed relative to the selected R wave portion to simulate the endogenous afferent activity occurring at a particular time in the cardiac cycle. In various embodiments, the delay has a duration less than about 500 milliseconds. In further embodiments, the delay has a duration less than about 1000 milliseconds.

In various embodiments, each of the microbursts occurs after an R-R interval (i.e., the amount of time between two successive R wave portions in the cardiac signal) having a duration that is shorter than the duration of the previous R-R interval. In further embodiments, the microbursts are delivered to the vagus nerve after the R wave portions occurring during inspiration but not after the R wave portions occurring during expiration.

The invention also includes a method of customizing the exogenous electrical signal to elicit a desired vagal evoked potential in a selected structure of the brain associated with a medical condition. The method includes determining a value of a signal parameter (e.g., pulse width, pulse frequency, an interpulse interval between two of the pulses of the microburst, microburst frequency, a number of microbursts of the series of microburst, a duration of the electrical signal, a number of pulses in the microbursts, etc.), generating an electrical signal having a series of microbursts of 2 to 20 electrical pulses each according to the signal parameter, delivering the electrical signal to the patient's vagus nerve, analyzing an EEG of the patient's brain created during the delivery of the electrical signal to determine the vagal evoked potential observed in the selected structure of the brain, and modifying the value of the signal parameter based on the vagal evoked potential observed in the selected structure of the brain to modify the vagal evoked potential observed therein. In various embodiments, the selected structure of the brain includes the thalamus, striatum, and/or insular cortex.

Embodiments of the invention also include a computer readable medium having computer executable components for detecting the QRS wave portion of the cardiac cycle, generating a microburst, and delivering the microburst to the vagus nerve of a patient in response to the detection of the QRS wave portion of the patient's cardiac cycle.

The invention also includes embodiments wherein the patient manually triggers the generation and delivery of the inventive exogenous electrical signal to his/her vagus nerve.

BRIEF DESCRIPTION OF THE SEVERAL VIEWS OF THE DRAWING(S)

Figure 3A:
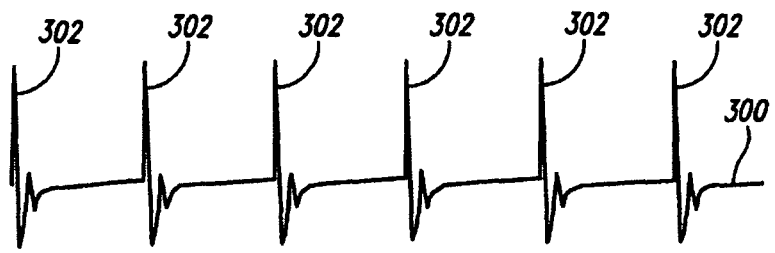
FIG. 3A is a trace illustrating an exemplary conventional VNS exogenous electrical signal having a series of pulses.
Figure 3B:
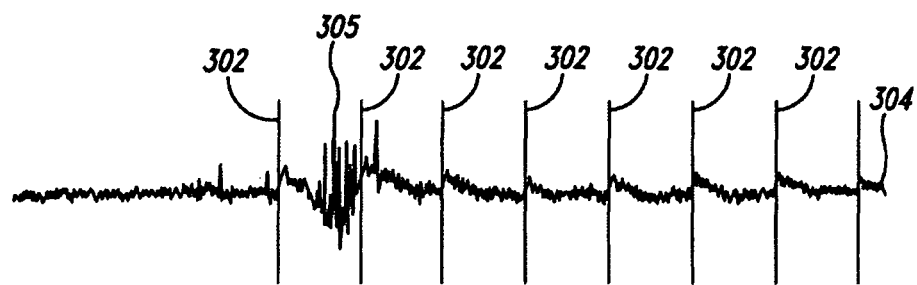
FIG. 3B is a trace of the potential measured in a monkey's thalamus while a portion of the conventional pulse burst of FIG. 3A was applied to the vagus nerve of the monkey.
Figure 3C:
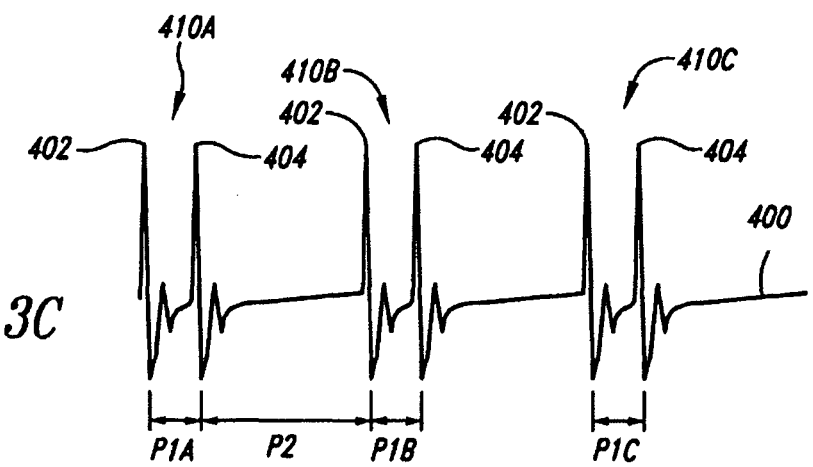
FIG. 3C is a trace illustrating an exemplary embodiment of an exogenous electrical signal constructed according to the present invention.
Figure 3D:
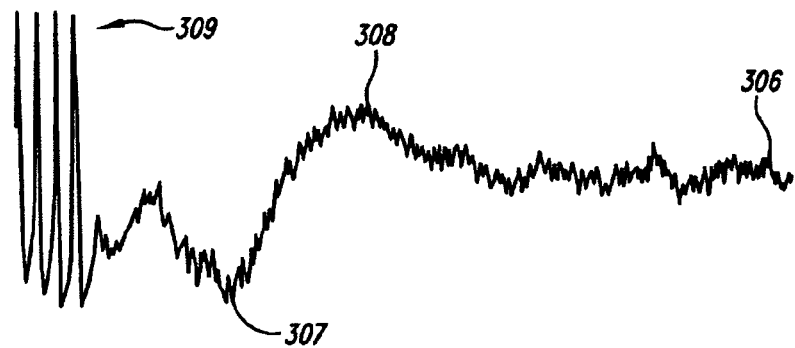

FIG. 3D is a trace illustrating the average potential (after 20 microbursts) measured in the monkey thalamus while a pulse burst having microbursts of four pulses each was applied to the vagus nerve. The inter-microburst interval was about 4 seconds and the interpulse interval was about 3 milliseconds.

Figure 3E:
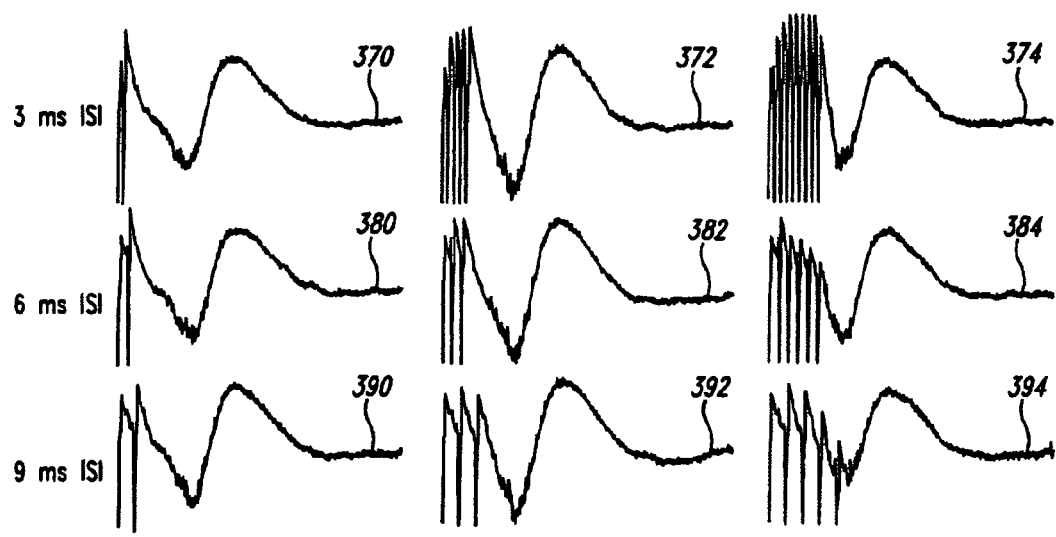

FIG. 3E provides nine exemplary traces of the potential measured inside a monkey's thalamus while various exogenous electrical signals were applied to the vagus nerve of the monkey. Each of the traces illustrates the average potential (after 20 microbursts) measured in the monkey thalamus while the exogenous electrical signals was applied to the monkey's vagus nerve. Each of the exogenous electrical signals included a series of microbursts having a selected number of pulses each. The pulses of the microbursts of the exogenous electrical signals of the topmost row have an interpulse interval of 3 milliseconds. The pulses of the microbursts of the exogenous electrical signals of the middle row have an interpulse interval of 6 milliseconds. The pulses of the microbursts of the exogenous electrical signals of the bottom row have an interpulse interval of 9 milliseconds.

Figure 3F:
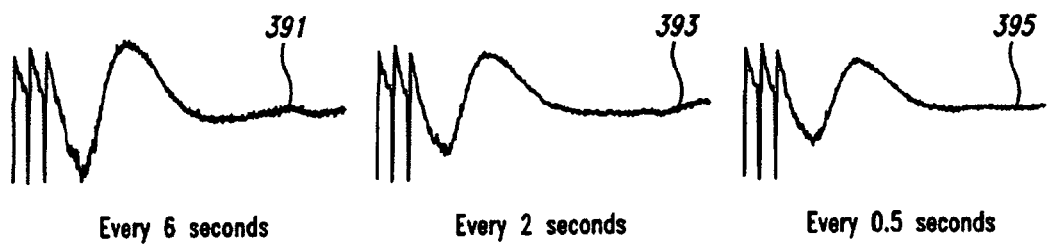

FIG. 3F provides three exemplary traces of the potential measured inside a monkey's thalamus while various exogenous electrical signals were applied to the vagus nerve of the monkey. Each of the traces illustrates the average potential (after 20 microbursts) measured in the monkey thalamus while the exogenous electrical signals was applied to the monkey's vagus nerve. All of the exogenous electrical signals included a series of microbursts having three pulses each. The pulses had an interpulse interval of 9 milliseconds. The exogenous electrical signal used to generate the leftmost trace included microbursts separated by an inter-microburst interval of about 6 seconds. The exogenous electrical signal used to generate the middle trace included microbursts separated by an inter-microburst interval of about 2 seconds. The exogenous electrical signal used to generate the rightmost trace included microbursts separated by an inter-microburst interval of about 0.5 seconds.

Figure 4A:
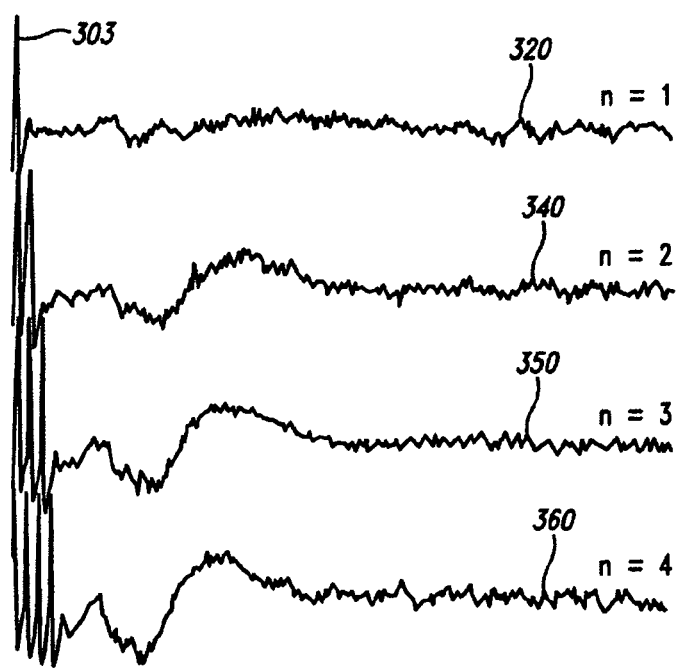

FIG. 4A provides four exemplary traces of the potential measured inside a monkey's thalamus while various exogenous electrical signals were applied to the vagus nerve of the monkey. For all of the exogenous electrical signals, the inter-microburst interval was about 4 seconds and the interpulse interval was about 3 milliseconds.

A topmost trace illustrates the average potential (after 20 pulses) measured in the monkey thalamus while a pulse burst having a series of uniformly spaced apart pulses was applied to the monkey's vagus nerve. The spacing between the pulses was about 4 seconds.

A second trace from the top depicts the average potential (after 20 microbursts) measured in the monkey thalamus while a pulse burst having microbursts of two pulses each was applied to the vagus nerve.

A third trace from the top depicts the average potential (after 20 microbursts) measured in the monkey thalamus while a pulse burst having microbursts of three pulses each was applied to the vagus nerve.

The bottommost trace depicts the average potential (after 20 microbursts) measured in the monkey thalamus while a pulse burst having microbursts of four pulses each was applied to the vagus nerve.

Figure 4B:
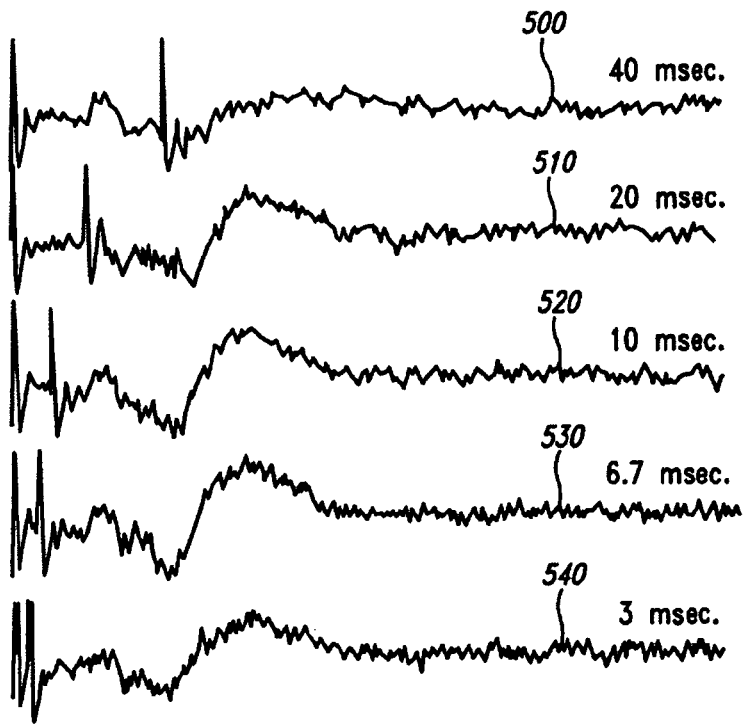

FIG. 4B provides five exemplary traces of the potential measured inside a monkey's thalamus while various exogenous electrical signals including microbursts having two pulses each, the microbursts being separated by an inter-microburst interval of about 4 seconds, were applied to the vagus nerve of the monkey. Each of the traces illustrates the average potential (after 20 microbursts) measured in the monkey thalamus while the exogenous electrical signals was applied to the monkey's vagus nerve.

The interpulse interval between the pulses of the microbursts of the exogenous electrical signal was about 40 milliseconds in the topmost trace.

The interpulse interval between the pulses of the microbursts of the exogenous electrical signal was about 20 milliseconds in the trace second from the top.

The interpulse interval between the pulses of the microbursts of the exogenous electrical signal was about 10 milliseconds in the trace third from the top.

The interpulse interval between the pulses of the microbursts of the exogenous electrical signal was about 6.7 milliseconds in the trace fourth from the top.

The interpulse interval between the pulses of the microbursts of the exogenous electrical signal was about 3 milliseconds in the bottommost trace.

Figure 4C:
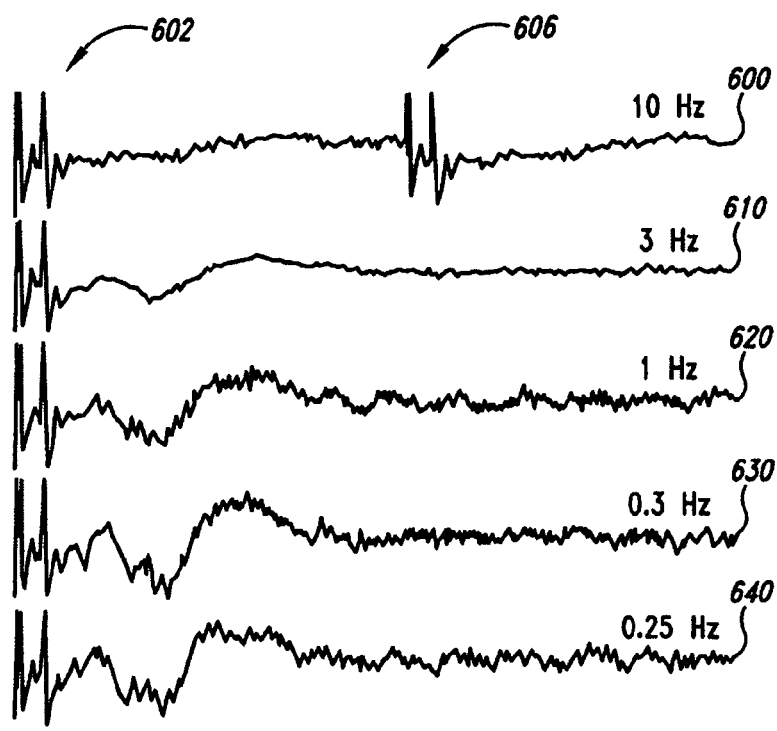

FIG. 4C provides five exemplary traces of the potential measured inside a monkey's thalamus while various exogenous electrical signals including microbursts having two pulses each, the pulses of each of the microbursts being separated by an interpulse interval of about 6.7 seconds, were applied to the vagus nerve of the monkey. Each of the traces illustrates the average potential (after 20 microbursts) measured in the monkey thalamus while the exogenous electrical signals was applied to the monkey's vagus nerve.

The inter-microburst interval between the microbursts of the exogenous electrical signal used in the topmost trace corresponded to the microbursts occurring at a microburst frequency of about 10 Hz.

The inter-microburst interval between the microbursts of the exogenous electrical signal used in the trace second from the top corresponded to the microbursts occurring at a microburst frequency of about 3 Hz.

The inter-microburst interval between the microbursts of the exogenous electrical signal used in the trace third from the top corresponded to the microbursts occurring at a microburst frequency of about 1 Hz.

The inter-microburst interval between the microbursts of the exogenous electrical signal used in the trace fourth from the top corresponded to the microbursts occurring at a microburst frequency of about 0.3 Hz.

The inter-microburst interval between the microbursts of the exogenous electrical signal used in the bottommost trace corresponded to the microbursts occurring at a microburst frequency of about 0.25 Hz.

Figure 5:
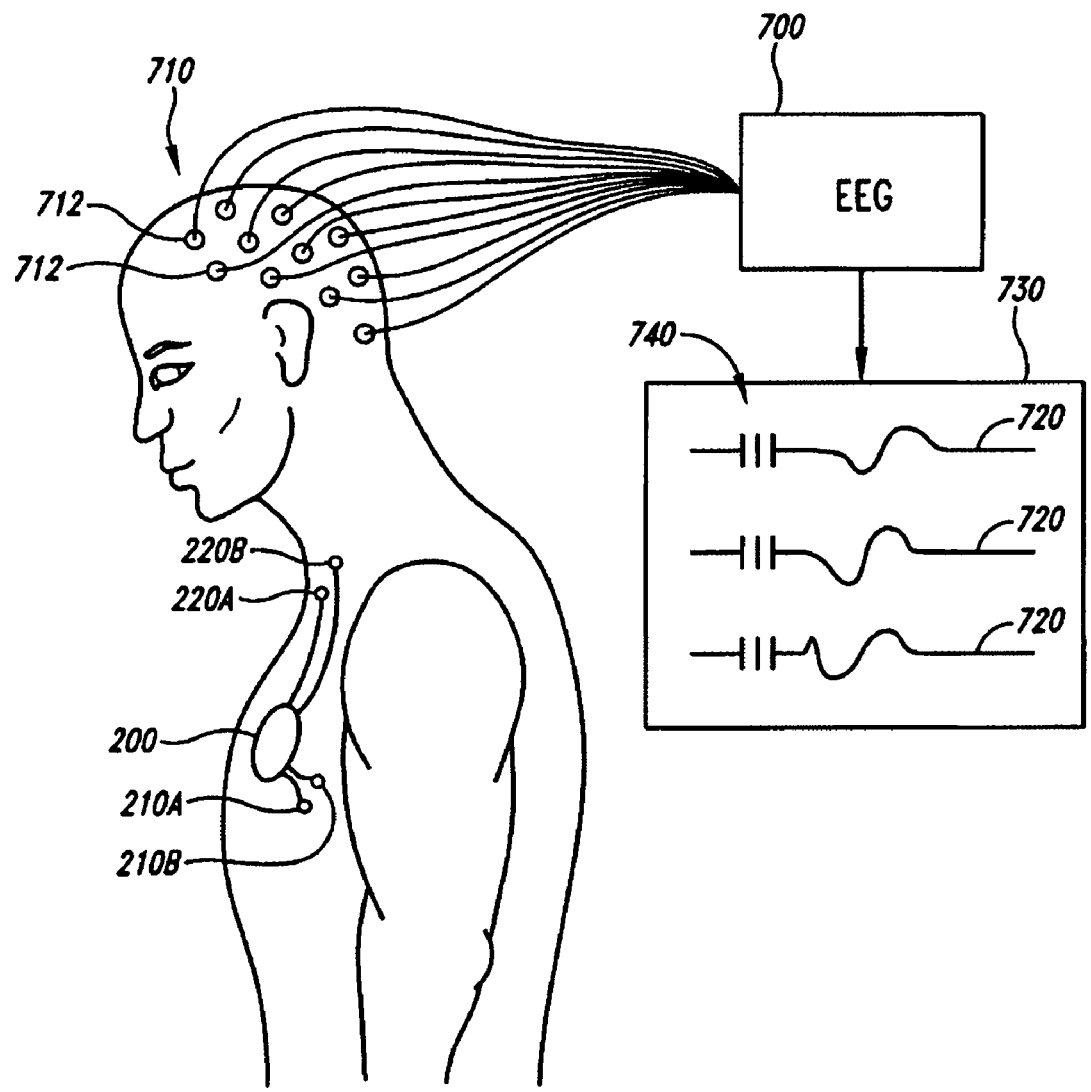

FIG. 5 illustrates a system for using a conventional EEG device to optimize an exogenous electrical signal used for VNS stimulation according to the present disclosure.

Figure 6:
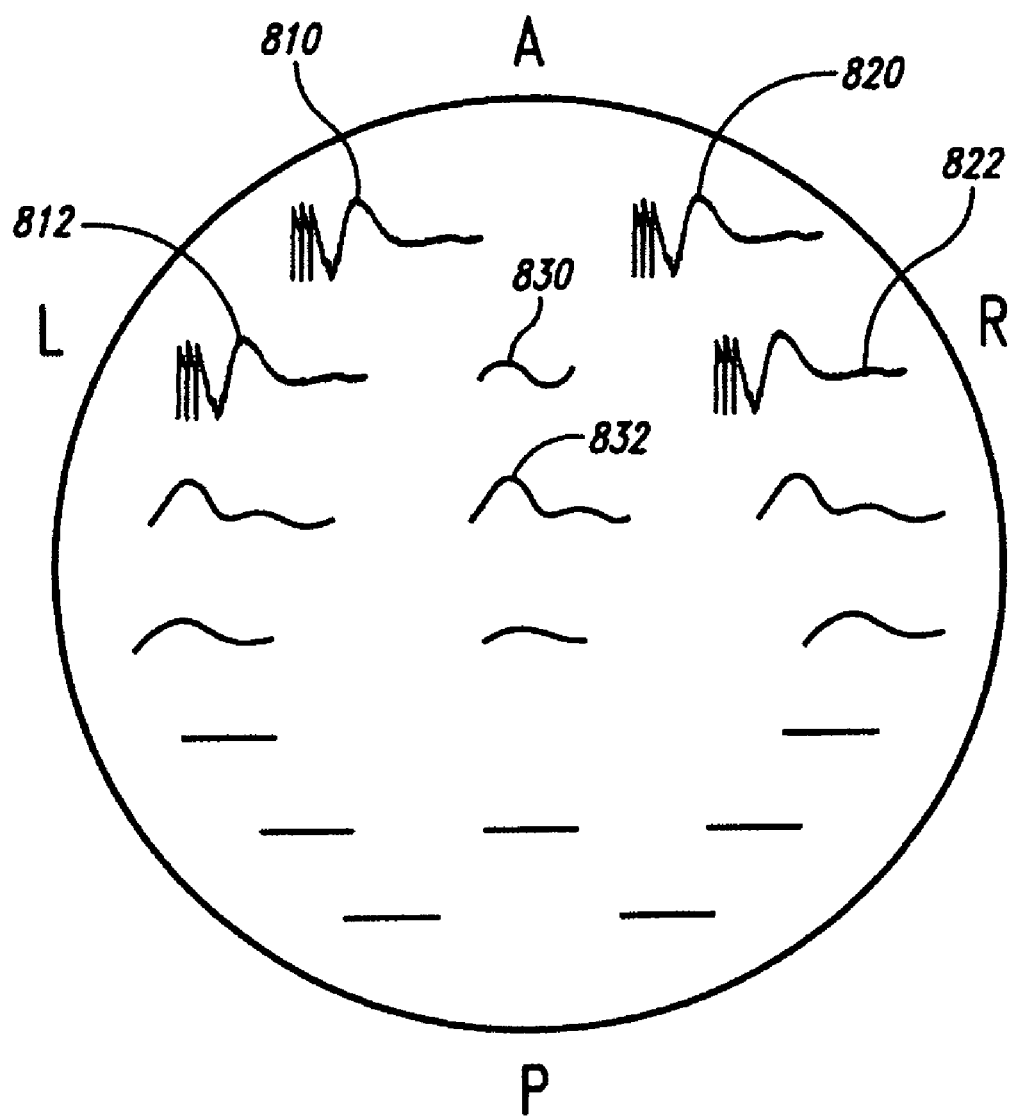

FIG. 6 provides an exemplary EEG illustrating the vagal evoked potential elicited by an exogenous electrical signal constructed according to the present invention.

Figure 2A:
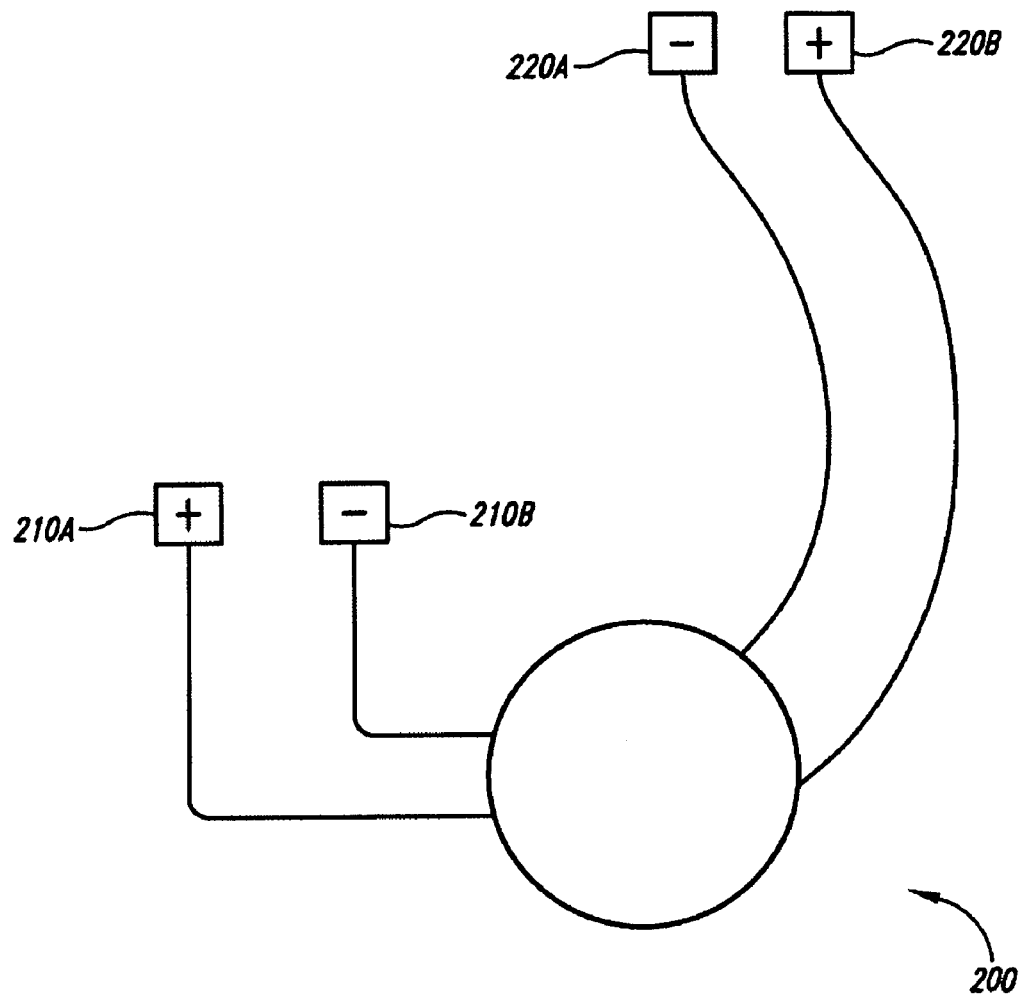
FIG. 2A illustrates a conventional electrical signal generator that may be modified to deliver an exogenous electrical signal constructed according to the present invention.
Figure 2B:
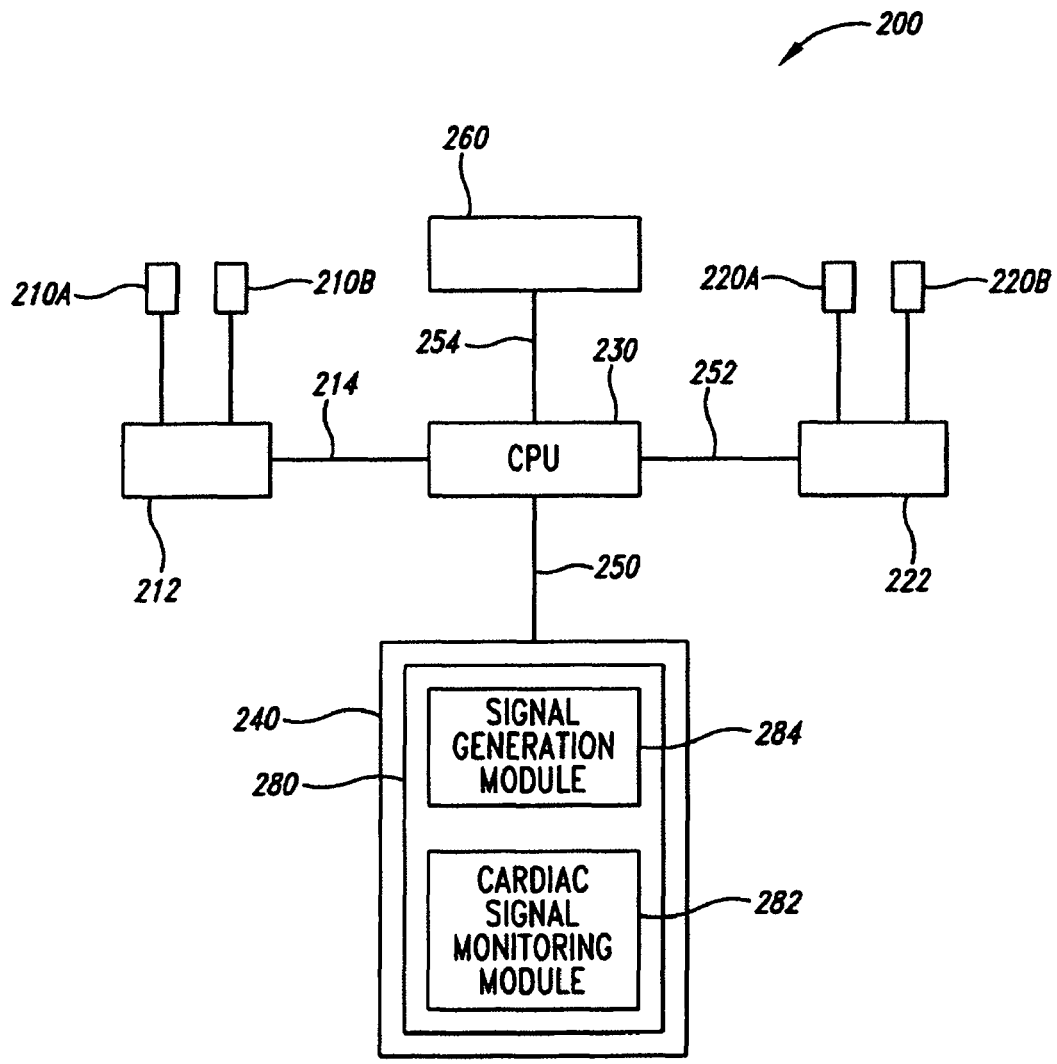
FIG. 2B is a block diagram illustrating various components of the electrical signal generator of FIG. 2A.
Figure 7:
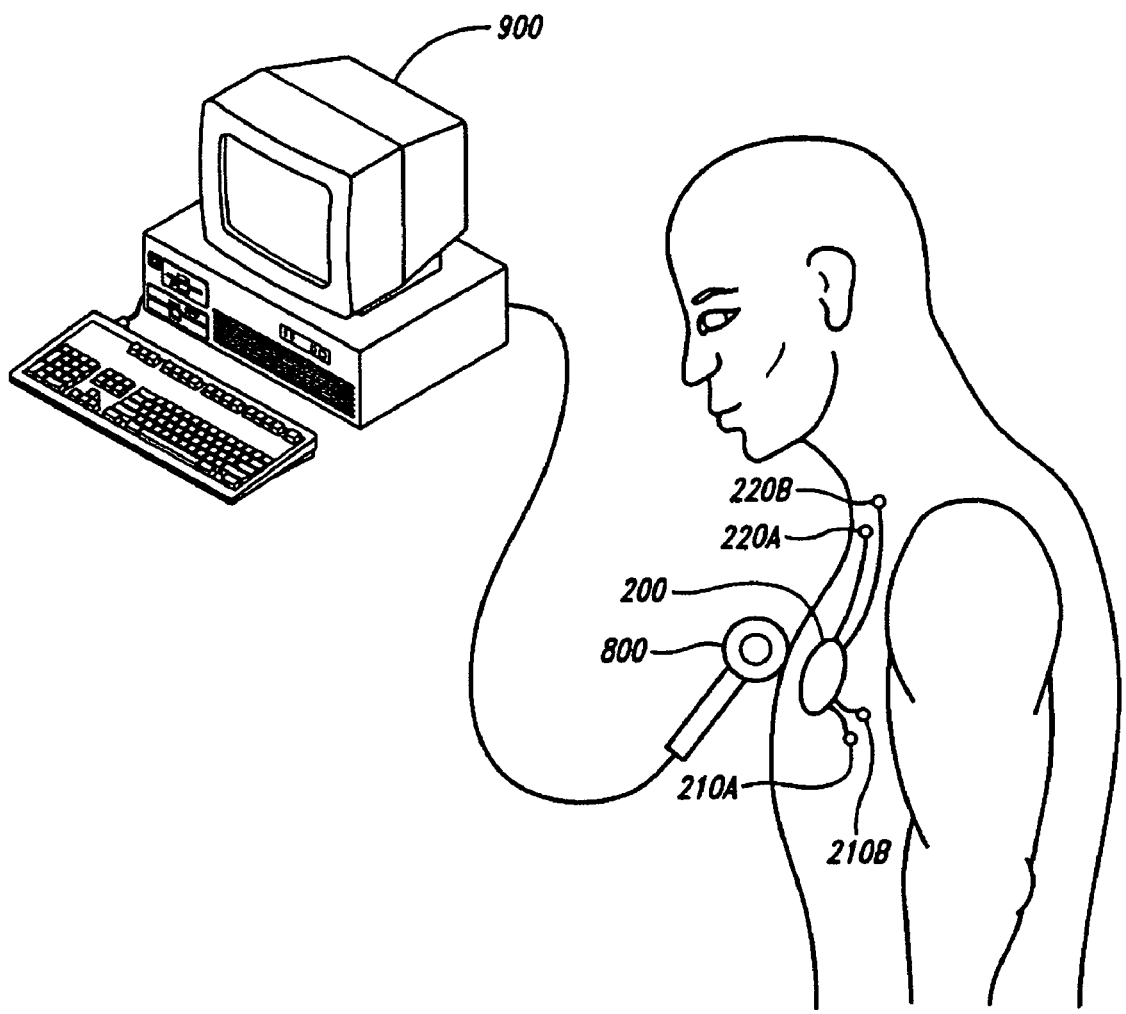

FIG. 7 illustrates an exemplary embodiment of an electrical signal generator programming and/or reprogramming device for use with the electrical signal generator of FIG. 2A-2B.

DETAILED DESCRIPTION OF THE INVENTION

The present invention provides novel techniques, alone or in combination, to improve the efficacy of VNS used in the treatment of a variety of medical conditions, including disorders of the nervous system, such as epilepsy and depression. The following disclosure describes various embodiments of a novel method and its associated apparatus for improving VNS therapies. According to the present disclosure, these novel techniques are particularly useful for treating epilepsy and depression. However, it is envisioned that these same novel techniques may be used to treat a variety of disorders and conditions that include a physiological relationship to the nervous system, such as neuropsychiatric disorders, eating disorders/obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including infertility). Thus, based on the aforementioned relationship to the nervous system, these disorders and conditions, including epilepsy and depression, are collectively referred to herein as disorders of the nervous system, even if not conventionally described as such.

One of the novel techniques includes synchronizing portions of an exogenous electrical signal with the endogenous afferent activity of the vagus nerve, primarily the endogenous afferent activity originating from receptors in the heart and lungs. Stimulating the vagus nerve in synchrony with endogenous vagal rhythms, in particular with cardiac cycle and heart rate variability (HRV), enhances therapeutic efficacy of VNS.

In the prior art, the exogenous electrical signal applied to the vagus nerve during conventional VNS is often referred to as a pulse burst. The pulse burst typically includes a series of uniformly spaced apart substantially identical pulses, i.e., a simple pulse train. The VNS applied to treat disorders of the nervous system may include multiple pulse bursts separated by an interburst delay.

An individual pulse burst may be triggered automatically or manually. In many prior art devices, a pulse burst may be triggered by the detection of a medical event such as a seizure, or may be triggered manually by the user or a medical professional. Alternatively, pulse bursts may occur at regular intervals separated by a predetermined interburst delay. Typically, the interburst delay is about five minutes, 30 minutes, or 60 minutes.

The pulses of the conventional VNS pulse bursts are applied asynchronously, i.e., asynchronous with both the cardiac and lung cycles. As mentioned above, conventional VNS is generally applied every 5 minutes in a 7 second to one minute pulse burst (see FIG. 3A for a portion of an exemplary burst) of uniformly spaced apart pulses having an pulse current amplitude of about 0.5 mA to about 2.0 mA. The pulses are delivered at about 20 Hz to about 50 Hz. Each of the pulses may have a width of about 0.5 milliseconds. While monophasic pulses are generally used, biphasic pulses may also be used. As used herein, the term "pulses" refers to both monophasic and biphasic pulses.

In the present invention, the pulses within a pulse burst are patterned or otherwise organized to improve and/or optimize stimulation of the vagus nerve and/or structures of the brain in communication therewith. The natural endogenous afferent activity in the left and right vagus nerves predominantly occurs immediately following each cardiac contraction and during each inspiration. Further, the timing of the endogenous afferent activity in the left and right vagus nerves varies with heart rate, breathing rate, and emotional state. However, because the left and right vagus nerves innervate different portions of the heart, the timing of the afferent activity in the left vagus nerve may differ from the timing of the afferent activity in the right vagus nerve. Consequently, the patterning of the pulse burst may be different for the right and left vagus nerves. As is appreciated by those of ordinary skill in the art, the pulse burst is generally applied to the left vagus nerve because VNS stimulators implanted on the right side applying a pulse burst to the right vagus nerve are associated with an increase in patient mortality. As used herein, the term "vagus nerve" may refer to either the left or right vagus nerve.

According to one aspect of the present invention, a novel exogenous electrical signal is applied to the vagus nerve. The novel exogenous electrical signal is configured to augment the natural endogenous afferent activity in the vagus nerve by timing the pulses within a pulse burst in an improved and more effective manner. In particular embodiments, as will be described in detail below, the pulses within the pulse burst may be organized into sub-bursts or microbursts (each having about 2 to about 20 pulses) that are synchronized with the endogenous afferent activity in the vagus nerve to augment the endogenous afferent activity therein.

Figure 1:
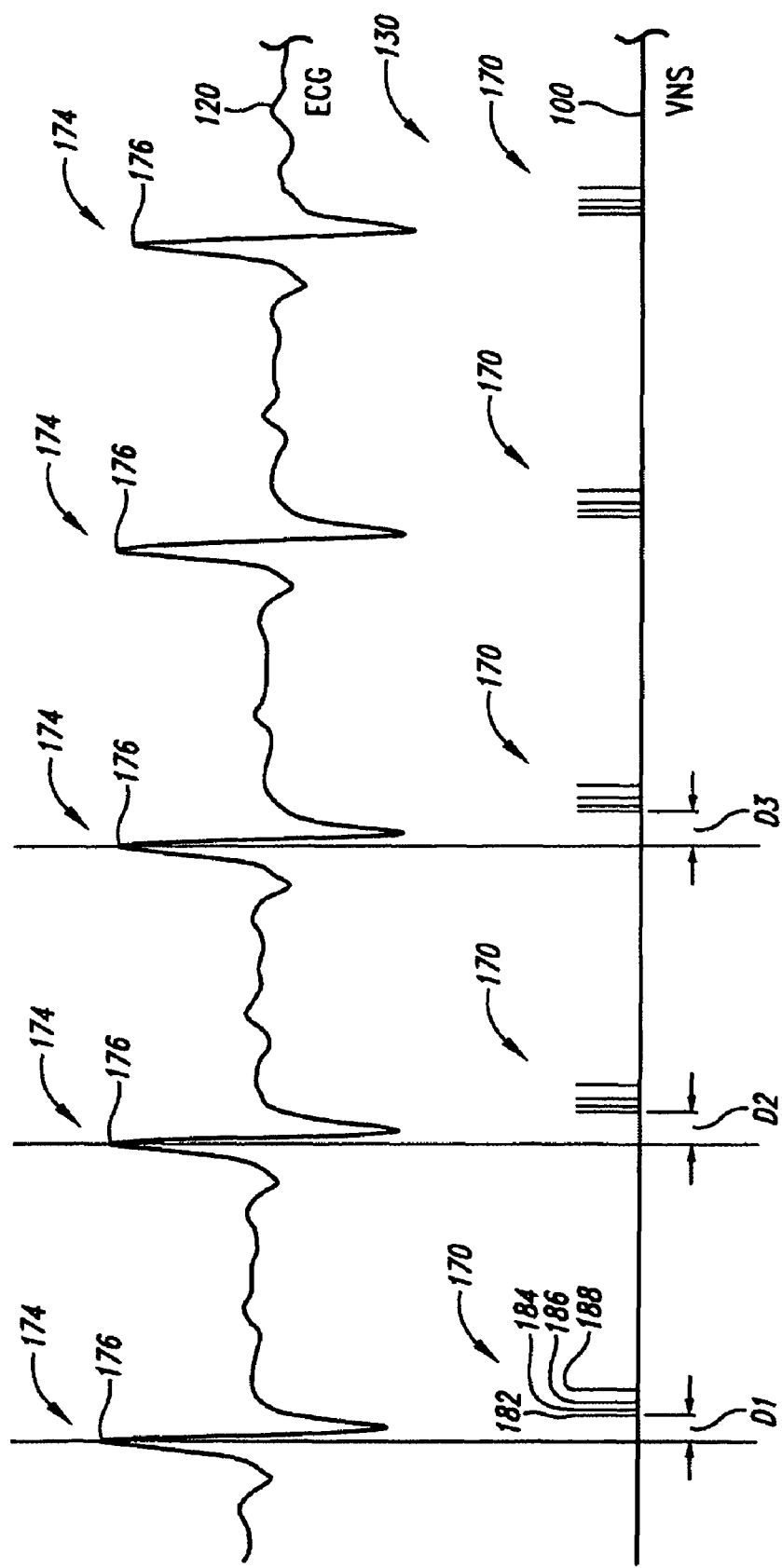
FIG. 1 illustrates a portion of an ECG trace located above a portion of a trace illustrating an exogenous electrical signal patterned into microbursts that are synchronized with the QRS wave portion of the ECG trace. Each of the microbursts begins after a delay period following the QRS wave portion of the ECG trace.

Referring to FIG. 1, a trace 100 of a portion of an exemplary embodiment of the novel exogenous electrical signal is provided. Located above the trace 100 in FIG. 1, an exemplary electrocardiogram (ECG) trace 120 depicting cardiac activity detected by an electrocardiograph (not shown) is provided. The novel exogenous electrical signal includes a pulse burst 130 organized into a series of microbursts 170. Each of the microbursts 170 is synchronized with a portion of the cardiac cycle depicted in the ECG trace 120. In particular, each of the microbursts 170 is synchronized with the QRS wave portion 174 of the ECG trace 120, so that endogenous cardiac-related and respiration-related vagal afferent activity is augmented by the microbursts 170 of the exogenous electrical signal.

As illustrated in FIG. 1, each of the microbursts 170 may be triggered by an R-wave portion 176 of the QRS wave portion 174. Without being bound by theory, it is believed that synchronizing the application of the microbursts 170 of the exogenous electrical signal to the vagus nerve with the detection of the R-wave portion 176 of the patient's cardiac cycle may increase the efficacy of VNS therapy by entraining the exogenous electrical signal with the endogenous cyclic facilitation of central vagal afferent pathways. Each of the microbursts 170 begins after the elapse of a delay period, which comprises a variable time period that may range, e.g., from about 10 milliseconds to about 1000 milliseconds following detection of the R-wave portion 176. In various embodiments, the delay period may be less than about 10 milliseconds. Further, in some embodiments, the delay period may be about 10 milliseconds to about 500 milliseconds or about 10 milliseconds to about 800 milliseconds. In further embodiments, the delay period is less than 1000 milliseconds. In other embodiments, the delay period may be omitted. Each of the delay periods may comprise a predetermined duration such as about 10 milliseconds, or may comprise a random time duration within a predetermined minimum and maximum time duration, e.g., a random time duration from about 10 milliseconds to about 1000 milliseconds. Further, as will be described below, the duration of the delay period preceding each microburst 170 may be determined empirically.

For example, the leftmost (first) microburst 170 begins after a delay period "D1," the next (or second) microburst 170 begins after a delay period "D2," and the third microburst 170 begins after a delay period "D3." The delay period "D1" may be shorter than the delay periods "D2" and "D3." Additionally, the delay period "D2" may be shorter than the delay period "D3." In alternate embodiments, the delay periods "D1," "D2," and "D3" may be substantially identical. In further embodiments, the delay period "D1," may be larger than delay period "D2," which may be larger than delay period "D3." Embodiments wherein each of the delay periods "D1," "D2," and "D3" is selected randomly within a specified range of delay values or determined empirically are also within the scope of the present invention. As will be appreciated by those of skill in the art, still further embodiments of the present invention may include a variety of delay period combinations that can be identified and implemented by routine experimentation. Each of these is considered to be within the scope of the present invention. While three delay periods have been described with respect to FIG. 1, it is apparent to those of ordinary skill that a delay period may precede each microburst of a pulse burst and the duration of the delay period may be determined empirically or randomly.

In various embodiments, the synchronization of the exogenous electrical signal further comprises not providing pulses during selected portions of the cardiac cycle, such as periods in the opposite half of the cardiac and respiratory duty cycles, when the central pathways are inhibited. Again without being bound by theory, it is believed that pulses applied to the vagus nerve during the opposite half of the cardiac and respiratory duty cycles are less effective because endogenous signals in this part of the cardiac and/or respiratory cycles are less significant, in terms of their information content, for modulating those portions of the brain relevant to homeostasis mechanisms implicated in medical conditions such as epilepsy and depression. Thus, at least a portion of the asynchronous exogenous electrical signal delivered by current stimulation algorithms, such as conventional VNS, may be therapeutically irrelevant.

Because the exogenous electrical signal is typically delivered by an implanted device powered by a battery, the delivery of irrelevant signals may result in unnecessary battery depletion. Further, the pulse burst sometimes causes the patient's vocal cords to contract causing his/her voice to become horse, which is uncomfortable and makes talking difficult. Sometimes, the pulse burst causes neck pain and may cause cardiac problems. Therefore, reducing the number of pulses may contribute to patient comfort and/or safety.

Synchronizing the microbursts 170 of the exogenous electrical signal with each individual QRS wave portion 174 also tracks the natural variability in vagal afferent activity that occurs during breathing and emotional shifts. This heart rate variability (HRV) is a function of respiration and efferent sympathovagal tone. During inspiration, the heart rate accelerates and during expiration it decelerates. Thus, an R-R interval (i.e., the time that elapses between successive R wave portions 176) appearing in the ECG is shorter during inspiration and longer during expiration, producing HRV. HRV is also known as respiratory sinus arrhythmia. Additionally, it is well established that a larger HRV is associated with greater physical health, including greater immune function, lower risk of cardiac arrhythmia, and better mood, than a smaller HRV.

HRV is greatly increased during meditation, and HRV is increased easily by slow, paced breathing. Synchronizing the microbursts 170 of the exogenous electrical signal with each QRS wave portion 174 of the cardiac cycle utilizes and accentuates the positive association of HRV with overall bodily health. Further, it helps ensure that the microbursts 170 of the exogenous electrical signal are synchronized with variances in the cardiac cycle. Consequently, it may be beneficial for the patient to begin paced breathing during the pulse burst. Further, it may improve the efficacy of the exogenous electrical signal if the pulse burst is triggered while the patient is performing paced breathing.

Referring to FIG. 2A-2B, a suitable electrical signal generator 200, such as a VNS stimulator, known in the art has one or more electrodes 220A and 220B coupled to the vagus nerve for delivering electrical pulses thereto. In embodiments wherein the microbursts of the exogenous electrical signal are synchronized with the cardiac cycle, optionally, the electrical signal generator 200 has the capacity to detect cardiac signals and produce an ECG trace for the purpose of avoiding the deliverance of conventional VNS in the event of cardiac arrest. In other words, the suitable electrical signal generator 200 for use with the present invention may include one or more sensors, such as sensing electrodes 210A and 210B positioned to detect cardiac electrical signals, and the onboard capability of analyzing those signals. In particular, the electrical signal generator 200 may be capable of identifying the R wave portion of the cardiac signal. In alternative embodiments, the sensor(s) may include an acoustic device configured to detect the cardiac cycle.

In embodiments wherein the microbursts of the exogenous electrical signal are synchronized with the cardiac cycle, the electrical signal generator 200 may be modified or programmed to deliver the novel exogenous electrical signal. The modifications include replacing a more common open-loop or non-feedback stimulation system with a feedback system utilizing one or more sensing electrodes 210A and 210B to detect the QRS wave portion 174 of the ECG trace 120 (see FIG. 1). The modification of the electrical signal generator 200 is effected by programming the electrical signal generator 200 to initiate a microburst 170 after the elapse of the delay period, such as delay period "D1", delay period "D2", or delay period "D3," following the detection of the QRS wave portion 174. Again, while three exemplary delay periods have been described, a delay period may precede each microburst and such embodiments are within the scope of the present invention. Further, embodiments in which no delay period precedes a microburst are also within scope of the present invention. As is apparent to those of ordinary skill in the art, embodiments of the electrical signal generator 200 that have the feedback system for detecting the QRS wave portion 174 without modification are also within the scope of the present invention.

FIG. 2B is a block diagram of various components of the electrical signal generator 200. The electrical signal generator 200 may include a programmable central processing unit (CPU) 230 which may be implemented by any known technology, such as a microprocessor, microcontroller, application-specific integrated circuit (ASIC), digital signal processor (DSP), or the like. The CPU 230 may be integrated into an electrical circuit, such as a conventional circuit board, that supplies power to the CPU 230. The CPU 230 may include internal memory or memory 240 may be coupled thereto. The memory 240 is a computer readable medium that includes instructions or computer executable components that are executed by the CPU 230. The memory 240 may be coupled to the CPU 230 by an internal bus 250.

The memory 240 may comprise random access memory (RAM) and read-only memory (ROM). The memory 240 contains instructions and data that control the operation of the CPU 230. The memory 240 may also include a basic input/output system (BIOS), which contains the basic routines that help transfer information between elements within the electrical signal generator 200. The present invention is not limited by the specific hardware component(s) used to implement the CPU 230 or memory 240 components of the electrical signal generator 200.

The electrical signal generator 200 may also include an external device interface 260 permitting the user or a medical professional to enter control commands, such as a command triggering the delivery of the novel exogenous electrical signal, commands providing new instructions to be executed by the CPU 230, commands changing parameters related to the novel exogenous electrical signal delivered by the electrical signal generator 200, and the like, into the electrical signal generator 200. The external device interface 260 may include a wireless user input device. The external device interface 260 may include an antenna (not shown) for receiving a command signal, such as a radio frequency (RF) signal, from a wireless user input device such as a computer-controlled programming wand 800 (see FIG. 7). The electrical signal generator 200 may also include software components for interpreting the command signal and executing control commands included in the command signal. These software components may be stored in the memory 240.

The electrical signal generator 200 includes a cardiac signal interface 212 coupled to sensing electrodes 210A and 210B for receiving cardiac electrical signals. The cardiac signal interface 212 may include any standard electrical interface known in the art for connecting a signal carrying wire to a conventional circuit board as well as any components capable of communicating a low voltage time varying signal received from the sensing electrodes 210A and 210B through an internal bus 214 to the CPU 230. The cardiac signal interface 212 may include hardware components such as memory as well as standard signal processing components such as an analog to digital converter, amplifiers, filters, and the like.

The electrical signal generator 200 includes an exogenous electrical signal interface 222 coupled to electrodes 220A and 220B for delivering the exogenous electrical signal to the vagus nerve. The exogenous electrical signal interface 222 may include any standard electrical interface known in the art for connecting a signal carrying wire to a conventional circuit board as well as any components capable of communicating a low voltage time varying signal generated by the CPU 230 or a signal generating device controlled by the CPU 230 to the electrodes 220A and 220B through an internal bus 252. The exogenous electrical signal interface 222 may include hardware components such as memory as well as standard signal processing components such as a digital to analog converter, amplifiers, filters, and the like.

The various components of the electrical signal generator 200 may be coupled together by the internal buses 214, 250, 252, and 254. Each of the internal buses 214, 250, 252, and 254 may be constructed using a data bus, control bus, power bus, I/O bus, and the like.

The electrical signal generator 200 may include instructions 280 executable by the CPU 230 for processing and/or analyzing the cardiac electrical signals received by the sensing electrodes 210A and 210B. Additionally, the electrical signal generator 200 may include instructions 280 executable by the CPU 230 for generating an exogenous electrical signal delivered to the vagus nerve by the electrodes 220A and 220B. These instructions may include computer readable software components or modules stored in the memory 240. The instructions 280 may include a Cardiac Signal Monitoring Module 282 that generates a traditional ECG trace from the cardiac electrical signals. The Cardiac Signal Monitoring Module 282 may record the ECG trace in the memory 240.

As is appreciated by those of ordinary skill in the art, generating an ECG trace from an analog cardiac electrical signal may require digital or analog hardware components, such as an analog to digital converter, amplifiers, filters, and the like and such embodiments are within the scope of the present invention. In one embodiment, some or all of these components may be included in the cardiac signal interface 212. In an alternate embodiment, some or all of these components may be implemented by software instructions included in the Cardiac Signal Monitoring Module 282. The Cardiac Signal Monitoring Module 282 may include any method known in the art for generating an ECG trace from a time varying voltage signal.

As mentioned above, the unmodified electrical signal generator 200 monitors cardiac electrical signals for the purposes of detecting a cardiac arrest. The Cardiac Signal Monitoring Module 282 may be modified to include instructions for detecting or identifying the R wave portion of the ECG trace. The R wave portion of the ECG trace may be detected using any method known in the art. While the electrical signal generator 200 has been described as having the Cardiac Signal Monitoring Module 282, embodiments in which the functionality of the Cardiac Signal Monitoring Module 282 is performed by more than one software component are within the scope of the present invention.

The unmodified electrical signal generator 200 generates the exogenous electrical signal used by conventional VNS. The instructions 280 include a Signal Generation Module 284 for instructing the CPU 230 how and when to generate the conventional VNS exogenous electrical signal and deliver it to the vagus nerve via the electrodes 220A and 220B. The Signal Generation Module 284 may be modified to generate the inventive novel exogenous electrical signal. Specifically, the Signal Generation Module 284 may be modified to include instructions directing the CPU 230 to synchronize the microbursts of the exogenous electrical signal with the R wave portion of the ECG trace. The Signal Generation Module 284 may determine the values of the various parameters used to define the novel exogenous electrical signal based on simulating the endogenous afferent activity of the vagus nerve as described herein. Alternatively, the values of the various parameters may be stored in the memory 240 and used by the Signal Generation Module 284 to generate the novel exogenous electrical signal. The various parameters may be entered into the memory 240 by the external device interface 260 which permits the user or medical professional to enter control commands, including commands changing parameters related to the novel exogenous electrical signal delivered by the electrical signal generator 200, and the like, into the electrical signal generator 200.

While the electrical signal generator 200 has been described as having the Signal Generation Module 284, embodiments in which the functionality of the Signal Generation Module 284 is performed by more than one software component are within the scope of the present invention.

Examples of suitable electrical signal generators for use with the present invention include a model 103 VNS stimulator (formally referred to as the Gen39) produced by Cyberonics, Inc. (Houston, Tex.), model 104 VNS stimulator also produced by Cyberonics, Inc., and the like. The analog recording and ECG recognition capacity of these VNS stimulators enable their onboard processor to be programmed to produce pulse bursts of vagal stimulation having the desired parameters at variable delay periods following the detection of the R-wave of the ECG. The delay periods may comprise a predetermined, programmable duration such as about 10 milliseconds, or may comprise a random time duration within a predetermined programmable minimum and maximum time duration, e.g., a random time duration from about 10 milliseconds to about 1000 milliseconds. The predetermined, programmable duration(s) of the delay period(s) may be determined empirically using methods described below.

While a relatively sophisticated embodiment of the electrical signal generator 200 is described above, those of ordinary skill appreciate that simpler devices, such as a device configured to deliver the exogenous electrical signal asynchronously (i.e., an exogenous electrical signal having microbursts that are not synchronized with the cardiac cycle) are also within the scope of the present invention. The electrical signal generator 200 may provide an asynchronous exogenous electrical signal having microbursts spaced at regular or variable intervals. For example, the microbursts may occur at least every 100 milliseconds or at the microburst frequency of about 0.25 Hz to about 10 Hz. The pulses within the microbursts may be spaced at regular or variable intervals. Further, less sophisticated embodiments of the electrical signal generator 200 include electrical signal generators that are pre-programmed with the exogenous electrical signal parameters (e.g., pulse width, pulse frequency, interpulse interval(s), microburst frequency, number of pulses in the microbursts, etc.) before implementation and may retain those pre-programmed parameter values throughout the functional life of the electrical signal generator. Alternatively, electrical signal generators configured to generate an asynchronous exogenous electrical signal may be programmable after implementation. For example, the computer-controlled programming wand 800 (see FIG. 7) may be used in the manner described above to program such electrical signal generators. As is readily apparent to those of ordinary skill, the present invention is not limited by the particular electrical signal generator used to generate the inventive exogenous electrical signal.

In one aspect, the microbursts of the exogenous electrical signal may be delivered following every detected R-wave occurring within a predetermined pulse burst period, i.e., the period of time during which the exogenous electrical signal is generated. In another embodiment, the microbursts may be applied to the vagus nerve only during the inspiratory phase. This may be implemented by programming the electrical signal generator 200 to apply a microburst only on the shortening R-R intervals during HRV, i.e., only on an R-wave having an R-R interval less than the preceding R-R interval, or less than a moving average for several R-R intervals, e.g., less than a 5 or 10 R-R interval moving average. In further embodiments, the electrical signal generator 200 may include a sensor, such as a strain gauge or acoustic device, that detects various biometric parameters such as heartbeat and the respiratory cycle. For example, a strain gauge may be used to determine inspiration is occurring by identifying when the chest is expanding. The invention is not limited by the method used to determine inspiration is occurring, the R-R interval, and/or whether the R-R intervals are shortening for the purposes of determining inspiration is occurring.

The timing parameters defining how the microbursts of the exogenous electrical signal are synchronized with the cardiac cycle for maximal therapeutic efficacy may be determined empirically, and according to particular embodiments, are individually optimized for each patient (as described below). In alternate embodiments, patients may perform paced breathing, e.g., taking a breath at a frequency of about 0.1 Hz, during periods when the exogenous electrical signal is being delivered to the vagus nerve, to facilitate or increase the amount of HRV.

In further embodiments, the various parameters of the cardiac cycle synchronized exogenous electrical signal may be varied, including without limitation the duration of the pulse burst, the delay period(s) following R-wave detection, the number of pulses comprising a microburst, the interpulse interval (i.e., the amount of time separating one pulse from an adjacent pulse), and the inter-microburst interval (i.e., the amount of time between successive microbursts). Further, these parameters may be selectively associated with particular R-waves of the respiratory cycle, depending on the length of each preceding R-R-interval. In various embodiments, these parameters are empirically optimized for each patient.

In another aspect of the present invention, a method of providing an exogenous electrical signal capable of inducing a much larger vagal evoked potential (VEP) than that induced by conventional VNS is provided. The exogenous electrical signal provided to the vagus nerve comprises a pulse burst including a series of microbursts. As described above the inter-microburst interval may be determined by the cardiac cycle.

An example of a portion of a pulse burst 300 used in conventional VNS may be viewed in FIG. 3A. The pulse burst 300 includes a plurality of uniformly spaced apart pulses 302 occurring about every 20 milliseconds to about every 50 milliseconds, i.e., occurring at a frequency of about 20 Hz to about 50 Hz. A conventional pulse burst, such as pulse burst 300 may have a pulse burst duration of about 7 seconds to about 60 seconds (resulting in a pulse burst having from about 140 to about 3000 pulses or more). Each pulse 302 may have a width or duration of about 50 microseconds to about 1000 microseconds (μsec) and a pulse current of about 0.1 mA to about 8 mA.

The pulse burst 300 may be separated from a pulse burst identical to pulse burst 300 by an interburst interval of about 5 min. Sometimes, an interburst interval of about 30 min. or about 60 min. is used. In further implementations, the pulse burst 300 is triggered by the onset of a medical event, such as a seizure, or is triggered by the user or a medical professional. In such embodiments, the interburst interval varies.

FIG. 3B provides a trace 304 of the potential measured in the monkey thalamus while the conventional pulse burst 300 (see FIG. 3A) of uniformly spaced pulses 302 having an interpulse interval of 4 seconds was applied to the vagus nerve. The trace 304 shows the potential inside the thalamus immediately after each of the pulses 302 is delivered to the vagus nerve. An increased VEP 305 occurs after the first pulse 302. However, as illustrated by FIG. 3B, little to no increased VEP is observed after the successive pulses 302 in the series. The average potential inside the thalamus observed over 20 pulses is provided by a topmost trace 320 in FIG. 4A. The VEP is the difference between a minimum average potential in the trace 320 observed after an averaged pulse portion 303 of the trace 320 and a maximum average potential in the trace 320 observed after the averaged pulse portion 303 of the trace 320. However, as illustrated in the trace 320, the minimum and the maximum potentials are not clearly identifiable.

Referring to FIG. 3C, a portion of a pulse burst 400 of the exogenous electrical signal constructed in accordance with the present invention is provided. As is apparent to those of ordinary skill, unlike the uniformly spaced pulses 302 of the pulse burst 300, the pulses 402 and 404 of the pulse burst 400 are patterned or structured within the pulse burst 400. Specifically, the pulses 402 and 404 are arranged into microbursts 410A, 410B, and 410C. In the embodiment depicted in FIG. 3C, each of the microbursts 410A, 410B, and 410C includes the pulse 402 followed by the pulse 404. Each of the individual pulses 402 and 404 in the pulse burst 400 resemble the pulses 302 of the conventional VNS pulse burst 300 and have a pulse width of about 50 microseconds to about 1000 microseconds (μsec) and a pulse current of about 0.25 mA to about 8 mA. In particular embodiments, the pulse current is less than about 2 mA.

While the individual pulses 402 and 404 in the pulse burst 400 resemble the pulses 302 of the conventional VNS pulse burst 300 (i.e., each has a pulse width of about 50 microseconds to about 1000 microseconds (μsec) and a pulse current of about 0.25 mA to about 8 mA) the number of pulses 402 and 404 in the pulse burst 400 is markedly smaller than the number of pulses 302 in the pulse burst 300, assuming the pulse burst 400 has the same duration as the pulse burst 300. As mentioned above, the conventional pulse burst 300 may have a pulse burst duration of about 7 seconds to about 60 seconds and a pulse frequency of about 20 Hz to about 50 Hz, resulting in a pulse burst having from about 140 to about 3000 pulses or more. If the pulse burst 400 has a duration of about 7 seconds to about 60 seconds, and the microbursts are delivered every 0.5 seconds, roughly corresponding to the interval between heart beats during inspiration, the pulse burst 400 will have about 30 pulses to about 242 pulses.

As mentioned above, reducing the number of pulses delivered to the vagus nerve may help prolong battery life as well as improve patient comfort and safety. Further, patterning the pulses of the pulse burst 400 into microbursts, such as microbursts 410A, 410B, and 410C increases the VEP observed in the brain. Because the VEP is increased, the current amplitude may be reduced, further increasing patient comfort and/or safety. The increased VEP may also improve the therapeutic effects of the exogenous electrical signal.

Referring to FIG. 3D, a trace 306 illustrating the average potential inside the monkey thalamus observed over a series of 20 microbursts, each having a series of four pulses with a 3 milliseconds interpulse interval separating the pulses, is provided. The microbursts of FIG. 3D are separated by a 4 second inter-microburst interval. The VEP is the difference between a minimum 307 in the trace 306 observed after an averaged microburst portion 309 of the trace 306 and a maximum 308 in the trace 306 observed after the averaged microburst portion 309 of the trace 306. The difference between the minimum 307 and the maximum 308 of the trace 306 is clearly larger than the difference between the unidentifiable minimum and the unidentifiable maximum of the trace 320 (see FIG. 4A and the pulse intervals after the third pulse in FIG. 3B). Therefore, without changing any parameters other than the number of pulses delivered every 4 sec., i.e., delivering a microburst instead of a single pulse, the VEP potential can be increased or enhanced.

The pulses 402 and 404 within the first microburst 410A are separated by an interpulse interval "P1A." The pulses 402 and 404 within the second microburst 410B are separated by an interpulse interval "P1B." The pulses 402 and 404 within the third microburst 410C are separated by an interpulse interval "P1C." In most cases, the interpulse intervals "P1A," "P1B," and "P1C" separating the pulses 402 and 404 are shorter than the interpulse intervals between the pulses 302 used in conventional VNS therapy. The first interpulse interval "P1A" may range from about one millisecond to about 50 milliseconds. Typically, the first interpulse interval "P1A" may range from about 2 milliseconds to about 10 milliseconds. In some embodiments, Typically, the first interpulse interval "P1A" may range from about 3 milliseconds to about 10 milliseconds. In various embodiments, the interpulse interval "P1B" may be substantially equal to the interpulse interval "P1A." Subsequent interpulse intervals occurring after the interpulse interval "P1B," such as interpulse interval "P1C," may be substantially equal to the interpulse interval "P1B." in alternate embodiments, the interpulse interval "P1A" may be larger than the interpulse interval "P1B," which may be larger than the interpulse interval "P1C." In further embodiments, the interpulse interval "P1A" may be smaller than the interpulse interval "P1B," which may be smaller than the interpulse interval "P1C." In various embodiments, the interpulse intervals "P1A," "P1B," and "P1C" may be selected randomly from a predetermined range of interpulse interval values. In further embodiments, the interpulse intervals may be variable and determined empirically, as described below.

The first microburst 410A is separated from the microburst 410B by an inter-microburst interval "P2." Each microburst may be considered an event occurring at a microburst frequency (i.e., the inverse of the sum of the inter-microburst interval "P2" and the duration of the microburst). The microburst frequency may range from about 0.25 Hz to about 10 Hz. It may be beneficial to use a microburst frequency that approximates the R-R cycle of the patient.

In various embodiments, the pulses within a microburst may be patterned or structured. For example, referring to FIG. 1, the portion of the pulse burst 130 is provided. The pulse burst 130 includes five microbursts 170, each triggered by the R-wave portion 176 of the cardiac cycle depicted in the ECG trace 120. Each microburst 170 includes four pulses 182, 184, 186, and 188. The first pulse 182 begins after the predetermined delay time "D1" has elapsed following the identification of the R-wave portion 176. The pulse 184 follows the pulse 182 after a first interpulse delay has elapsed. Then, after a second interpulse interval, the pulse 186 is generated. Finally, after a third interpulse interval, the pulse 188 is generated. In the embodiment depicted in FIG. 1, the interpulse intervals increase in duration along the series of pulses. However, the interpulse intervals may be determined empirically and individualized for each patient. While each microburst 170 in FIG. 1 has only four pulses, microbursts 170 having 2 to 20 pulses, and consequently 1 to 19 interpulse intervals, are within the scope of the present invention. In some embodiments, the microbursts 170 may have 2 to 15 pulse, or alternatively, 3 to 6 pulses.

In various embodiments, the pulse burst 400 may be separated from a pulse burst identical to pulse burst 400 or a dissimilar pulse burst by an interburst interval of about 5 minutes to about 240 minutes. Alternatively, the interburst interval may be about 200 milliseconds to about 24 hours. In further embodiments, the pulse burst is applied continuously. The pulse burst may have a duration of about 100 milliseconds to about 60 minutes. In various embodiments, the pulse burst duration is determined empirically for a particular patient and/or medical condition. In further embodiments, the pulse burst 400 is triggered by the onset of a medical event, such as a seizure, or is triggered by the user or a medical professional. In such embodiments, the interburst interval varies. Optionally, the pulse burst 400 may be terminated automatically by the onset of a medical event, such as cardiac arrest, or manually the user or a medical professional. In such embodiments, the pulse burst duration varies.

Pulses, such as pulses 182, 184, 186, and 188, arranged into microbursts, such as microburst 170, are capable of evoking an enhanced vagal evoked potential (eVEP) in the patient's brain that is significantly greater than an VEP evoked by conventional VNS (see FIG. 3A). However, this eVEP may attenuate as the number of pulses within a microburst increases beyond an optimal number of pulses. Framed a little differently, the eVEP attenuates as the microburst duration increases beyond an optimal duration. Thus, for example, where a microburst exceeds 2 pulses to 5 pulses, the eVEP begins to diminish, and if more than 20 pulses are provided, the eVEP essentially disappears. This may be observed in FIG. 3E.

Referring to the top row of FIG. 3E, traces 370, 372, and 374 illustrate the average potential inside the monkey thalamus averaged over a series of 20 microbursts, each having a series of pulses separated by an interpulse interval of 3 milliseconds. The microbursts of FIG. 3E are separated by a 4 second inter-microburst interval. The number of pulses within the microbursts increase from left to right. In the leftmost trace 370, the microbursts had 2 pulses each. In the center trace 372, the microbursts had 5 pulses each. And, in the rightmost trace 374, the microbursts had 9 pulses each. Again, the VEP observed in each trace, is the difference between a minimum in the trace observed after an averaged microburst portion (appearing at the left of the trace) and a maximum in the trace observed after the averaged microburst portion of the trace. The top row clearly illustrates that using these parameters, microbursts having 5 pulses produce a larger VEP than microbursts having 2 pulses. However, microbursts having 9 pulses produce a smaller VEP than microbursts having 5 pulses.

Referring to the middle row of FIG. 3E, traces 380, 382, and 384 illustrate the average potential inside the monkey thalamus averaged over a series of 20 microbursts, each having a series of pulses separated by an interpulse interval of 6 milliseconds. In the leftmost trace 380, the microbursts had 2 pulses each. In the center trace 382, the microbursts had 3 pulses each. And, in the rightmost trace 384, the microbursts had 6 pulses each. The middle row clearly illustrates that using these parameters, microbursts having 3 pulses produce a larger VEP than microbursts having 2 pulses. However, microbursts having 6 pulses produce a smaller VEP than microbursts having 3 pulses.

Referring to the bottom row of FIG. 3E, traces 390, 392, and 394 illustrate the average potential inside the monkey thalamus averaged over a series of 20 microbursts, each having a series of pulses separated by an interpulse interval of 9 milliseconds. In the leftmost trace 390, the microbursts had 2 pulses each. In the center trace 392, the microbursts had 3 pulses each. And, in the rightmost trace 394, the microbursts had 5 pulses each. The bottom row clearly illustrates that using these parameters, microbursts having 3 pulses produce a larger VEP than microbursts having 2 pulses. However, microbursts having 5 pulses produce a smaller VEP than microbursts having 3 pulses.

Referring to the leftmost column of FIG. 3E, traces 370, 380, and 390 illustrate the facilitation the first pulse provides to the second pulse of the microburst. The traces 372, 382, and 392 in the rightmost column of FIG. 3E illustrate additional facilitation provided by adding additional pulses to the microburst. However, the traces 374, 384, and 394 in the rightmost column of FIG. 3E illustrate that if the duration of the microbursts is too long, the microburst extends into an inhibitory period of neural activity reducing the VEP observed in the thalamus of the monkey. Consequently, the VEP may be improved and/or optimized by the selection of the number of pulses of the microbursts.

It may be helpful to define a microburst by its duration rather than the number of pulses. Experimental results related to optimizing microburst duration are illustrated in FIGS. 3E and 4B. For example, ignoring the pulse widths, FIG. 3E illustrates that the VEP begins to decline when the sum of the interpulse intervals within a single microburst exceeds about 30 milliseconds. Consequently, for the monkey, the optimal sum of the interpulse intervals within a single microburst may be less than 30 milliseconds and in some embodiments, less than 20 milliseconds. The data of FIG. 3E further indicates, a range of about 12 milliseconds to about 18 milliseconds may be used. Human beings are larger and have a heart rate that is roughly half (about 180 beats/minute for the monkey and about 70 beats/minute for a human). Therefore, one of ordinary skill will recognize that by doubling the sum of the interpulse intervals, the sum of the interpulse intervals may be converted for use with a human. Based on this rough approximation, for humans, the optimal sum of the interpulse intervals within a single microburst may be less than 80 milliseconds and in some embodiments, the sum may be less than 60 milliseconds. In further embodiments, the sum of the interpulse intervals within a single microburst may be less than about 40 milliseconds and preferably about 12 milliseconds to about 40 milliseconds. In some embodiments, the sum of the interpulse intervals within a single microburst may be about 10 milliseconds to about 80 milliseconds. One of ordinary skill in the art will also recognize alternate methods of converting the sum of the interpulse intervals determined in the experimental monkey data for use with a human and that such embodiments are within the scope of the present invention. Further, the sum of the interpulse intervals for use with a human may be determined empirically using the empirical method described below.

Generally, the microburst duration (i.e., the sum of the interpulse intervals and the pulse widths within a microburst) may be less than about one second. In particular embodiments, the microburst duration may be less than about 100 milliseconds. In particular embodiments, microbursts having a duration of about 4 milliseconds to about 40 milliseconds may be used.

Referring to the top row of FIG. 3F, traces 391, 393, and 395 illustrate the average potential inside the monkey thalamus averaged over a series of 20 microbursts, each having a series of pulses separated by an interpulse interval of about 9 milliseconds. The microbursts used to create the traces 391, 393, and 395 are separated by about a 6 second, about a 2 second, and about a 0.5 second inter-microburst interval, respectively. While the VEP in the trace 395 is less than the VEP in the other two traces 393, and 395, the trace 395 illustrates that the eVEP is present at the rate the QRS wave occurs in the cardiac cycle during inspiration, i.e., about once every 0.5 second. Consequently, microbursts synchronized with the QRS wave during inspiration may produce eVEP in the thalamus and other brain structures in electrical communication therewith. Other parameters, such as interpulse interval(s), delay period(s), pulse current amplitude, pulse width, pulse burst duration, and the like may be adjusted to improve and/or optimize the VEP.

To maintain the eVEP, the present invention provides a microburst having only a small number of pulses as well as an inter-microburst interval that serves as a period during which the vagus nerve (and/or brain structures in communication therewith) may recover from the microburst. Providing an appropriate inter-microburst interval helps ensure that the succeeding microburst in the pulse burst of the exogenous electrical signal is capable of generating the eVEP. In some embodiments, the inter-microburst interval is as long as or longer than the duration of the microburst. In another embodiment, the inter-microburst interval is at least 100 milliseconds. In further embodiments, the inter-microburst interval may be as long as 4 seconds or 6 seconds. In some embodiments, the inter-microburst interval may be as long as 10 seconds. Each microburst comprises a series of pulses that, in some embodiments, are intended to mimic the endogenous afferent activity on the vagus nerve. In one embodiment, the microburst may simulate the endogenous afferent vagal action, such as the action potentials associated with each cardiac and respiratory cycle.

The central vagal afferent pathways involve two or more synapses before producing activity in the forebrain. Each synaptic transfer is a potential site of facilitation and a non-linear temporal filter, for which the sequence of inter-microburst intervals and/or interpulse intervals within a microburst can be optimized. Without being bound by theory, it is believed that the use of microbursts enhances VNS efficacy by augmenting synaptic facilitation and "tuning" the input stimulus train to maximize the forebrain evoked potential.

FIG. 4A-4C illustrate the effects of modifying the various parameters of the exogenous electrical signal on the VEP measured in the thalamus of a monkey. FIG. 4A illustrates the effects of varying the number of pulses in a microburst. FIG. 4B illustrates the effects of varying the interpulse interval between the pulses of a microburst having only two pulses. FIG. 4C illustrates the effects of varying the inter-microburst interval between adjacent microbursts having only two pulses each.

The topmost trace 320 of FIG. 4A provides the average potential (after 20 pulses) measured in the monkey thalamus while a pulse burst of uniformly spaced apart pulses having an interpulse interval of 4 seconds was applied to the vagus nerve.

A trace 340 of FIG. 4A depicts the average potential (after 20 microbursts) measured in the monkey thalamus while a pulse burst having microbursts of two pulses each was applied to the vagus nerve. The inter-microburst interval was about 4 seconds and the interpulse interval was about 3 milliseconds. The VEP (i.e., the difference between the minimum and maximum potentials observed after each microburst) is noticeably improved in the trace 340 when compared with the VEP of the trace 320.

A trace 350 depicts the average potential (after 20 microbursts) measured in the monkey thalamus while a pulse burst having microbursts of three pulses each was applied to the vagus nerve. The inter-microburst interval was about 4 seconds and the interpulse interval was about 3 milliseconds. The VEP is noticeably improved in the trace 350 when compared with the VEP of the trace 340.

A trace 360 depicts the average potential (after 20 microbursts) measured in the monkey thalamus while a pulse burst having microbursts of four pulses each was applied to the vagus nerve. The inter-microburst interval was about 4 seconds and the interpulse interval was about 3 milliseconds. The VEP is noticeably improved in the trace 360 when compared with the VEP of the trace 350.

Referring to FIG. 4B, the effect of the interpulse interval on the VEP is illustrated. Traces 500, 510, 520, 530, and 540 depict the average potential (after 20 microbursts) measured in the monkey thalamus while a pulse burst having microbursts of two pulses each, separated by an inter-microburst interval of 4 sec. was applied to the vagus nerve. The interpulse intervals were about 40 milliseconds, about 20 milliseconds, about 10 milliseconds, about 6.7 milliseconds, and about 3 milliseconds for the traces 500, 510, 520, 530, and 540, respectively. The VEP is barely visible in the trace 500. The VEP is noticeably improved in the trace 510 when compared with the VEP of the trace 500. The VEP is noticeably improved in the trace 520 when compared with the VEP of the trace 510. The VEP is noticeably improved in the trace 530 when compared with the VEP of the trace 520. However, the VEP in the trace 540 is noticeably less than the VEP 534 of the trace 530.

Referring to FIG. 4C, the effect of the inter-microburst interval on the VEP is illustrated. Traces 600, 610, 620, 630, and 640 depict the average potential (after 20 microbursts) measured in the monkey thalamus while a pulse burst having microbursts of two pulses each, the pulses being separated by an interpulse interval of 6.7 milliseconds. was applied to the vagus nerve. The inter-microburst intervals corresponded to the microbursts occurring at a microburst frequency of about 10 Hz, about 3 Hz, about 1 Hz, about 0.3 Hz, and about 0.25 Hz for the traces 600, 610, 620, 630, and 640, respectively. The VEP is barely visible in the trace 600. Because the inter-microburst internal was sufficiently short, the trace 600 shows a second microburst artifact 606 to the right of the first microburst artifact 602. The VEP is noticeably improved in the trace 610 when compared with the VEP of the trace 600. The VEP is noticeably improved in the trace 620 when compared with the VEP of the trace 610. The VEP is noticeably improved in the trace 630 when compared with the VEP of the trace 620. However, the VEP in the trace 640 is noticeably less than the VEP in the trace 630.

As depicted in FIG. 4A-4C, the VEP is enormously enhanced (resulting in eVEP) and optimized by using a microburst of pulses (two or more, FIG. 4A) at appropriate interpulse intervals (in this case, 6.7 milliseconds was optimal for the first interpulse interval, shown in FIG. 4B) and at a inter-microburst interval (i.e., microburst frequency) that approximates the R-R cycle (i.e., the frequency at which the R wave portion appears in the ECG trace) of the monkey (in this case, about 0.3 Hz, as shown in FIG. 4C).

The experimental results depicted in FIGS. 3D-3F and 4A-4C were obtained using a pulse burst including microbursts that were not synchronized with the cardiac cycle. In additional experiments, the effect of synchronizing the pulse bursts with the cardiac cycle was shown. Specifically, a single pulse was delivered at various times following every third R-wave. The VEP values obtained were then correlated with respiration. With respect to synchronization with the cardiac cycle, the experiments showed that the largest VEP was obtained when the pulse was delivered within 250 milliseconds after the initiation of a breath (which is accompanied by a decrease in the R-R interval). With respect to the delay period, the experiments showed that the greatest improvement in the VEP was obtained when the pulse was delivered about 400 milliseconds after the R-wave.

Additionally, the experimental data showed that by timing the pulse properly, an improvement in efficacy on the order of a factor of ten was obtained. Specifically, when the pulse was delivered about 0.5 seconds to about 1.0 second following the initiation of respiration and within 50 milliseconds following the R-wave, the VEP had a peak-to-peak amplitude of about 0.2 mV to about 0.4 mV. In contrast, when the pulse was delivered about 250 milliseconds after the initiation of inspiration and about 400 milliseconds following the R-wave, the VEP had a peak-to-peak amplitude of about 1.2 mV to about 1.4 mV. At maximum, this corresponds to about a sevenfold improvement in the VEP. These data show that by synchronizing the stimulation with respect to the cardiorespiratory cycles of the monkey, the efficacy of the stimulus pulse can be greatly improved over that of asynchronous stimulus delivery. These measurements were made in a monkey under deep anesthesia. Consequently, those of ordinary skill would expect an even greater effect in an awake human.

The use of pairs of pulses is a standard physiological tool for producing central responses by stimulation of small-diameter afferent fibers. However, according to the present invention, a pulse burst including microbursts of pulses having an appropriate sequence of interpulse intervals enormously enhances the effect of VNS. By selecting the appropriate signal parameters (e.g., pulse width, pulse frequency, interpulse interval(s), microburst frequency, microburst duration, number of pulses in the microbursts, etc.), the exogenous electrical signal applied to the vagus nerve may comprise a series of microbursts that each provide an eVEP.

As illustrated in FIGS. 4A and 3E, a microburst duration greater than about 10 milliseconds (corresponding to 4 pulses having an interpulse interval of about 3 milliseconds.) produces a maximal eVEP in the thalamus of the monkey and an interpulse interval of about 6 milliseconds to about 9 milliseconds produces maximal facilitation by the first pulse of the second pulse. Accordingly, a brief microburst of pulses with a total duration of about 10 milliseconds to about 20 milliseconds and having an initial interpulse interval of about 6 milliseconds to about 9 milliseconds and subsequent intervals of similar or longer duration may produce an optimal VEP. This is because such microbursts of pulses simulate the pattern of naturally occurring action potentials in the small-diameter afferent vagal fibers that elicit the central response that the present enhanced and optimized therapy is most interested in evoking (see below). Selection of an appropriate inter-microburst interval to separate one microburst from the next may be performed experimentally, although as previously noted, a period of at least 100 milliseconds (preferably at least 500 milliseconds, and more preferably at least one second) and at least equal to the microburst duration may be desirable.

The most effective sequence of interpulse intervals will vary with the patient's HRV (cardiac and respiratory timing) and also between individual patients, and thus, in some embodiments, the parameters of the exogenous electrical signal, such as the number of pulses in a microburst, the interpulse interval(s), the inter-microburst interval(s), the duration of the pulse burst, the delay period(s) between each QRS wave and a microburst, the current amplitude, the QRS waves of the cardiac cycle after which a microburst will be applied, the pulse width, and the like may be optimized for each patient. As a standard microburst sequence for initial usage, a microburst of 2 or 3 pulses having an interpulse interval of about 5 milliseconds to about 10 milliseconds may be used to approximate the short burst of endogenous post-cardiac activity.

The inter-microburst interval may be determined empirically by providing microbursts with a steadily decreasing inter-microburst interval until the eVEP begins to decline. In some embodiments, the interpulse interval varies between the pulses. For example, the interpulse interval may increase between each successive pulse in the microburst, simulating the pattern of a decelerating post-synaptic potential, as illustrated in FIG. 1. In alternative embodiments, the interpulse intervals may decrease between each successive pulse in the microburst, or may be randomly determined within a preselected range, e.g., about 5 milliseconds to about 10 milliseconds. Alternatively, the interpulse interval may remain constant between successive pulses in the microburst (i.e., providing a simple pulse train). Further, in a method described below, the interpulse intervals may be specified between each successive pair of pulses using the VEP determined by an EEG. These modifications to the conventional VNS methodology produce a significant enhancement of VNS efficacy that is applicable to all VNS protocols and to many different medical conditions, including disorders of the nervous system.

As noted above, the stimulation parameters (e.g., interpulse interval(s), inter-microburst interval(s), number of pulses per microburst, etc.) may be individually optimized for each patient. The optimization is accomplished by using surface electrodes to detect a far-field VEP, originating in the thalamus and other regions of the forebrain, and varying the stimulus parameters to maximize the VEP detected. As illustrated in FIG. 5, standard EEG recording equipment 700 and a 16-lead or a 25-lead electrode placement 710 of the EEG surface electrodes 712, such as that typically used clinically for recording somatosensory or auditory evoked potentials, enables the VEP present in the patient's forebrain to be detected, using VNS stimulus microburst timing to synchronize averages of about 8 epochs to about 12 epochs. The EEG recording equipment 700 may be used to produce continuous EEG waveforms 720 and recordings 730 thereof. By testing the effects of varying the parameters of the exogenous electrical signal, the VEP can be optimized for each patient.

The exogenous electrical signal used to deliver VNS is optimized in individual patients by selecting stimulus parameters that produce the greatest effect as measured by EEG surface electrodes 740. The pulse current amplitude and pulse width is first optimized by measuring the size of the VEP elicited by individual pulses (and not microbursts). The number of pulses, interpulse intervals, and inter-microburst intervals are then optimized (using the current amplitude and pulse width determined previously) by measuring the magnitude of the VEP evoked by the microbursts, as well as the effects on de-synchronization in the continuous EEG recordings. It may be desirable to determine the number of pulses first and then determine the interpulse intervals between those pulses. In alternate embodiments, it may be desirable to determine the number of pulses first, followed by the microburst duration, and lastly, the interpulse intervals between the pulses.

Because the large eVEPs recorded in the thalamus, striatum, and insular cortex of the anesthetized monkey and shown in FIG. 4A-4C, are large enough that if evoked in a human patient, the eVEPs are observable in a standard EEG detected using electrodes adjacent to the human patient's scalp, the standard EEG may be used to indicate the effects of modifications to the signal parameters of the exogenous electrical signal. In this manner, the EEG may be used to optimize or tune the signal parameters of the exogenous electrical signal empirically. For a human patient, this method provides a safe and non-invasive way to customize the various signal parameters for the patient and/or the treatment of the patient's medical condition.

The eVEP recorded in the right thalamus and right striatum is significant for the anti-epileptic effects of VNS, whereas the eVEP recorded in the left insular cortex is most significant for the anti-depression effects of VNS. By using regional EEG localization on the right or left frontal electrodes, the signal parameters of the exogenous electrical signal may be optimized appropriately to achieve an eVEP in the appropriate region of the individual patient's brain. Further, the magnitude of the measured VEP may be appropriately tuned for the patient.

The optimal exogenous electrical signal parameters for eliciting eVEPs from these two areas (right thalamus/striatum and left insular cortex, respectively) may differ. Both eVEPs are identifiable using known EEG recording methods in awake human patients. Therefore, EEG recordings made using these methods may be used to evaluate the eVEP in the appropriate area. The EEG recording may be used to collect samples of the eVEP in the appropriate area(s) and those samples may be used easily for a parametric optimization, in a patient suffering from a disorder of the nervous system such as epilepsy or depression. Similarly, the exogenous electrical signal parameters used for HRV-synchronization may be selected based on their effects on the VEP and on the heartbeat-related evoked potential both of which may be measured using known noninvasive EEG recording methods that use EEG electrodes attached to the patient's scalp.

Referring to FIG. 6, an exemplary EEG is provided. A pair of traces 810 and 812 correspond to the potential present in the left striatum and left insular cortex and a pair of traces 820 and 822 correspond to the potential present in the left striatum and left insular cortex. While the same traces 810, 812, 820 and 822 depict the potential present in striatum and insular cortex, the potential in the striatum may be distinguished from the potential in the insular cortex by its timing. Experiments have shown that pulses applied to the vagus nerve reach the parafascicular nucleus in the thalamus in about 18 milliseconds and the basal portion of the ventral medial nucleus in about 34 milliseconds. The parafascicular nucleus then projects the stimulus to the striatum and the basal portion of the ventral medial nucleus projects the stimulus to the insular cortex. Consequently, the potential evoked by the pulse burst in the striatum will appear in the traces 810, 812, 820 and 822 before the potential evoked in the insular cortex. By analyzing the traces 810, 812, 820 and 822, the potential inside the striatum and/or the insular cortex may be observed and the signal parameter used to generate those potentials modified to enhance and/or optimize those potentials.

In FIG. 6, the strong VEP shown in traces 820 and 822 corresponding to the right thalamus and the right striatum (or basal ganglia) is associated with the anti-epileptic effects of VNS. As mentioned above, distinguishing the right thalamus from the right insular cortex may be accomplished by analyzing the timing of the eVEP observed in the traces 820 and 822. The strong VEP shown in traces 810 and 812 corresponding to the left thalamus and left insular cortex is associated with the anti-depression effects of VNS. Traces 830 and 832 in the central portion of the EEG depict a weak VEP in the thalamus. Because the EEG method described is noninvasive, it offers a safe and effective method of enhancing and/or optimizing the therapeutic effects of the exogenous electrical signal.

FIG. 7 illustrates one method of variable programming of the electrical signal generator 200 to optimize the eVEP in the right thalamus and striatum for epileptic patients, and in the left insula for patients suffering from depression. As shown in FIG. 7, a computer 900 may be coupled to and used to program the computer-controlled programming wand 800. The programming wand 800 may use radio frequency telemetry to communicate with the electrical signal generator 200 and program the burst duration, number of pulses in a microburst, interpulse interval(s), pulse frequency, microburst duration, inter-microburst interval, pulse width, and current amplitude of the exogenous electrical signal delivered by the electrical signal generator 200 to the vagus nerve of the patient. Using the programming wand 800, programming may be performed periodically or as needed on an implanted electrical signal generator 200. This provides the ability to continually optimize and change the exogenous electrical signal delivered by the electrical signal generator 200 depending on the EEG, and to respond to changes therein. Therefore, the present method of using one or more of the above referenced techniques, alone or in combination, significantly enhances and/or optimizes currently available VNS therapies.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method of treating a brain disorder in a patient having a cardiac cycle, a vagus nerve, and a brain, the method comprising:
   detecting at least a portion of the cardiac cycle of the patient;
   applying to a selected location on the vagus nerve of the patient, in response to having detected the portion of the cardiac cycle of the patient, a pulsed electrical signal configured to increase afferent activity on the vagus nerve to be conducted thereby to the brain to treat the brain disorder, the pulsed electrical signal being selected from the group consisting of a single microburst and a plurality of microbursts, wherein each microburst of the pulsed electrical signal is applied to the selected location on the vagus nerve of the patient, and wherein each microburst of the pulsed electrical signal is patterned and comprises:
   from 2 to 6 pulses per microburst;
   at least one interpulse interval between adjacent pulses of the microburst, each interpulse interval ranging from about 5 to about 10 milliseconds; and
   a microburst duration less than or equal to 100 milliseconds.

2. The method of claim 1 wherein detecting the portion of the cardiac cycle of the patient comprises:
   detecting a portion of a QRS complex of the patient's cardiac cycle, and
   applying the pulsed electrical signal comprises synchronizing the application of the pulsed electrical signal to the vagus nerve of the patient with a QRS complex of the patient's cardiac cycle.

3. The method of claim 1 wherein detecting the portion of the cardiac cycle of the patient comprises detecting an R wave of the patient's cardiac cycle, and wherein applying the pulsed electrical signal comprises applying the pulsed electrical signal to the vagus nerve of the patient after a delay period following detection of each of a plurality of R waves of the patient.

4. The method of claim 3 wherein said delay period comprises from about 10 milliseconds to about 1000 milliseconds following detection of each of said plurality of R waves.

5. The method of claim 4 wherein said delay period comprises from about 10 milliseconds to about 500 milliseconds following detection of each of said plurality of R waves.

6. The method of claim 3 wherein said delay periods comprise random time periods within a specified range of delay values.

7. The method of claim 1 wherein the pulsed electrical signal comprises a plurality of microbursts, and wherein each microburst other than the last of said plurality of microbursts is separated from an adjacent microburst by an interburst period of from about 100 milliseconds to about six seconds.

8. The method of claim 1 wherein the pulsed electrical signal comprises a plurality of microbursts, and wherein the plurality of microbursts are applied to the vagus nerve at a microburst frequency of about 10 Hz to about 0.25 Hz.

9. The method of claim 1, further comprising:
   providing at least one electrode;
   providing at least one sensor;
   coupling the at least one electrode to the vagus nerve of the patient;
   providing an electrical signal generator coupled to the electrode;
   detecting the portion of the cardiac cycle of the patient using the at least one sensor;
   generating the pulsed electrical signal using the electrical signal generator; and
   applying the pulsed electrical signal to the at least one electrode.

10. The method of claim 1 wherein the brain disorder is selected from the group consisting of epilepsy, neuropsychiatric disorders including but not limited to depression, eating disorders including obesity, traumatic brain injury, coma, addiction disorders, dementia, sleep disorders, pain, and migraine.

11. The method of claim 1 wherein a sum of the interpulse intervals separating the pulses of each of the microbursts is less than about 60 milliseconds.

12. The method of claim 1 wherein the pulsed electrical signal is applied to augment natural endogenous afferent vagal activity.

13. The method of claim 1 further comprising not providing the pulsed electrical signal during at least a portion of the cardiac cycle of the patient.

14. The method of claim 1 wherein detecting the portion of the cardiac cycle of the patient comprises acoustically detecting at least a portion of the cardiac cycle of the patient.

15. The method of claim 1 further comprising:
   detecting at least a portion of a respiratory cycle of the patient;
   wherein applying the pulsed electrical signal to the vagus nerve further comprises applying the pulsed electrical signal in response to having detected the portion of the respiratory cycle of the patient.

16. The method of claim 1 wherein each microburst comprises from 3 to 5 pulses per microburst, wherein the at least one interpulse interval comprises a plurality of interpulse intervals, and wherein at least one interpulse interval of the plurality of interpulse intervals in each microburst is selectively varied from the other interpulse intervals.

17. A method of treating a medical condition in a patient having a cardiac cycle, a respiratory cycle, and a vagus nerve, the method comprising:
   detecting at least a portion of the cardiac cycle of the patient;
   detecting at least a portion of the respiratory cycle of the patient, wherein detecting the portion of the respiratory cycle of the patient comprises detecting one of an inspiration of breath and an expiration of breath; and
   in response to detecting the portion of the cardiac cycle of the patient and the portion of the respiratory cycle of the patient, applying a pulsed electrical signal to the vagus nerve of the patient, the pulsed electrical signal comprising a plurality of microbursts, wherein applying the pulsed electrical signal comprises applying a microburst to the vagus nerve of the patient after a delay period following the detection of one of the inspiration of breath and the expiration of breath, and wherein each microburst is separated from an adjacent microburst by an interburst period of at least 100 milliseconds and each microburst is characterized by:

from 2 to 20 pulses per microburst;
an interpulse interval between adjacent pulses of the microburst of from about 1 to about 20 milliseconds; and
a microburst duration of not greater than 1 second.

18. The method of claim 17 wherein the delay period following the detection of the one of the inspiration of breath and the expiration of breath is about 0.5 seconds to about 1.0 seconds after the detection of the inspiration of breath.

19. The method of claim 17 wherein applying the pulsed electrical signal comprises applying a microburst to the vagus nerve of the patient within about 250 milliseconds after the detection of the inspiration of breath.

20. A method of treating a medical condition in a patient having a cardiac cycle, a vagus nerve, and a brain, the method comprising:
applying a first pulsed electrical signal comprising a plurality of microbursts to the vagus nerve of the patient;
measuring a first enhanced Vagal Evoked Potential (eVEP) in a target area of the patient's brain;
changing at least one of a number of pulses per microburst, an interpulse interval between adjacent pulses of the microburst, a microburst duration, and an interburst period to provide a second pulsed electrical signal comprising a plurality of microbursts;
applying the second pulsed electrical signal to the vagus nerve of the patient;
measuring a second eVEP in the target area of the patient's brain;
comparing the first eVEP and the second eVEP;
selecting one of the first electrical signal and the second electrical signal for continued application to the vagus nerve of the patient based upon the comparing;
detecting at least a portion of the cardiac cycle of the patient; and
in response to detecting the portion of the cardiac cycle of the patient, applying the selected electrical signal to the vagus nerve of the patient, wherein each of the microbursts of the first and second electrical signals is separated from an adjacent microburst by an interburst period of at least 100 milliseconds and each microburst is characterized by:
from 2 to 20 pulses per microburst;
an interpulse interval between adjacent pulses of the microburst of from about 1 to about 20 milliseconds; and
a microburst duration of not greater than 1 second.

21. The method of claim 20 wherein the target area of the patient's brain is selected from the group consisting of the right thalamus, the right striatum, and the left insular cortex.

22. A method comprising:
for a patient having a brain, a vagus nerve, a cardiac cycle, and a neuropsychiatric disorder, detecting an R-wave of the cardiac cycle of the patient;
applying to a selected location on the vagus nerve of the patient, in response to having detected the R-wave of the cardiac cycle of the patient, a pulsed electrical signal configured to increase afferent activity on the vagus nerve to be conducted thereby to the brain to treat the neuropsychiatric disorder, the pulsed electrical signal being selected from the group consisting of a single microburst and a plurality of microbursts, wherein each microburst of the pulsed electrical signal is applied to the selected location on the vagus nerve of the patient, and wherein each microburst of the pulsed electrical signal is patterned and comprises:

from 2 to 6 pulses per microburst;
at least one interpulse interval between adjacent pulses of the microburst, each interpulse interval ranging from about 5 to about 10 milliseconds; and
a microburst duration less than or equal to 100 milliseconds.

23. The method of claim 22 wherein the neuropsychiatric disorder is depression.

24. A method of treating a brain disorder in a patient having a cardiac cycle, a vagus nerve, and a brain, the method comprising:
detecting at least a portion of the cardiac cycle of the patient;
applying to a selected location on the vagus nerve of the patient, in response to having detected the portion of the cardiac cycle of the patient, a pulsed electrical signal configured to increase afferent activity on the vagus nerve to be conducted thereby to the brain to treat the brain disorder, the pulsed electrical signal being selected from the group consisting of a single microburst and a plurality of microbursts, wherein each microburst of the pulsed electrical signal is applied to the selected location on the vagus nerve of the patient, and wherein each microburst of the pulsed electrical signal is patterned and comprises:
a plurality of pulses per microburst;
a plurality of interpulse intervals between adjacent pulses of the microburst, wherein each interpulse interval is between about 5 to about 10 milliseconds, and wherein at least one interpulse interval of the plurality of interpulse intervals in each microburst is selectively varied from the other interpulse intervals; and
a microburst duration less than or equal to 100 milliseconds.

25. The method of claim 24 wherein the plurality of pulses comprises between 3 and 20 pulses per microburst.

26. The method of claim 24 wherein detecting the portion of the cardiac cycle of the patient comprises:
detecting a portion of a QRS complex of the patient's cardiac cycle, and
applying the pulsed electrical signal comprises synchronizing the application of the pulsed electrical signal to the vagus nerve of the patient with a QRS complex of the patient's cardiac cycle.

27. The method of claim 24 wherein detecting the portion of the cardiac cycle of the patient comprises detecting an R wave of the patient's cardiac cycle, and wherein applying the pulsed electrical signal comprises applying the pulsed electrical signal to the vagus nerve of the patient after a delay period following detection of the R wave.

28. The method of claim 27 wherein said delay period comprises from about 10 milliseconds to about 1000 milliseconds following detection of the R wave.

29. The method of claim 27 wherein the pulsed electrical signal comprises a plurality of microbursts, wherein the step of applying the pulsed electrical signal comprises applying at least one of the plurality of microbursts to the vagus nerve of the patient after a delay period following detection of each of a plurality of R waves of the patient, and wherein said delay periods comprise random time periods within a specified range of delay values.

30. The method of claim 24 wherein detecting the portion of the cardiac cycle of the patient comprises detecting an T wave of the patient's cardiac cycle, and wherein applying the pulsed electrical signal comprises applying the pulsed electrical signal to the vagus nerve of the patient after a delay period following detection of the T wave.

* * * * *